US012595288B2

(12) United States Patent　(10) Patent No.:　US 12,595,288 B2

Gilles et al.　(45) Date of Patent:　Apr. 7, 2026

(54) VASOPRESSIN-2 RECEPTOR ANTAGONIST PEPTIDES AND USES THEREOF

(71) Applicant: COMMISSARIAT A L'ENERGIE ATOMIQUE ET AUX ENERGIES ALTERNATIVES, Paris (FR)

(72) Inventors: Nicolas Gilles, Gif sur Yvette (FR); Justyna Ciolek, Coignieres (FR); Laura Droctove, Paris (FR); Bernard Maillere, Gif sur Yvette (FR); Herve Nozach, Gif sur Yvette (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 591 days.

(21) Appl. No.: 18/002,625

(22) PCT Filed: Jun. 23, 2021

(86) PCT No.: PCT/EP2021/067248

§ 371 (c)(1), (2) Date: Dec. 20, 2022

(87) PCT Pub. No.: WO2021/260068

PCT Pub. Date: Dec. 30, 2021

(65) Prior Publication Data

US 2023/0234994 A1　　Jul. 27, 2023

(30) Foreign Application Priority Data

Jun. 24, 2020　(EP) ................................... 20305696

(51) Int. Cl.
*C07K 14/46*　(2006.01)
*A61K 38/17*　(2006.01)
*C12N 15/63*　(2006.01)
*G01N 33/50*　(2006.01)

(52) U.S. Cl.
CPC .............. *C07K 14/46* (2013.01); *A61K 38/17* (2013.01); *C12N 15/63* (2013.01); *G01N 33/5008* (2013.01); *G01N 2333/72* (2013.01)

(58) Field of Classification Search
CPC ........ C07K 14/46; A61K 38/17; C12N 15/63; G01N 33/5008; G01N 2333/72
See application file for complete search history.

(56) References Cited

U.S. PATENT DOCUMENTS

| | | |
|---|---|---|
| 2014/0341810 A1 | 11/2014 | North et al. |
| 2015/0252086 A1 | 9/2015 | Gilles et al. |
| 2017/0107292 A1 | 4/2017 | North et al. |

OTHER PUBLICATIONS

International Search Report issued Jul. 16, 2021 in PCT/EP2021/067248, filed on Jun. 23, 2021, 4 pages.
European Search Report issued Oct. 22, 2020 in European Application 20305696.5, filed on Jun. 24, 2020, 2 pages.

*Primary Examiner* — Li N Komatsu
(74) *Attorney, Agent, or Firm* — Oblon, McClelland, Maier & Neustadt, L.L.P.

(57) ABSTRACT

A peptide may include a sequence having 80% or more amino acid identity with the amino acid sequence of SEQ ID NO. 1, i.e., RPSX$_1$CNLPVKPGPCX$_2$ GFFSAFYYSQKX$_3$NKCHSFTYGGCAGNANRFSTX$_4$EKCRRTC X$_5$X$_6$, wherein, X$_1$ is the amino acid residue F or G, X$_2$ is any amino acid residue, except a basic amino acid residue, X$_3$ is the amino acid residue T or D, X$_4$ is the amino acid residue I, L, or E, (i) X$_5$ is V and X$_6$ is G or (ii) X$_5$ is G and X6 is V, and the amino acid located at position 39 is A. Such peptides may have various diagnostic and therapeutic uses.

14 Claims, 4 Drawing Sheets

Specification includes a Sequence Listing.

natremia

SEQUENCE LISTING

```
<160> NUMBER OF SEQ ID NOS: 25

<210> SEQ ID NO 1
<211> LENGTH: 57
<212> TYPE: PRT
<213> ORGANISM: Artificial Sequence
<223> OTHER INFORMATION: X1, X2, X3, X4, X5 and X6 are as defined.
<220> FEATURE:
<223> OTHER INFORMATION: X1, X2, X3, X4, X5 and X6 are as defined.
<220> FEATURE:
<221> NAME/KEY: VARIANT
<222> LOCATION: 4
<223> OTHER INFORMATION: X1 means the amino acid residue F or G
<220> FEATURE:
<221> NAME/KEY: VARIANT
<222> LOCATION: 15
<223> OTHER INFORMATION: X2 means any amino acid residue, excepted a
     basic amino acid
<220> FEATURE:
<221> NAME/KEY: VARIANT
<222> LOCATION: 27
<223> OTHER INFORMATION: X3 means the amino acid residue T or D
<220> FEATURE:
<221> NAME/KEY: VARIANT
<222> LOCATION: 48
```

```
<223> OTHER INFORMATION: X4 means the amino acid residue I, L or E
<220> FEATURE:
<221> NAME/KEY: VARIANT
<222> LOCATION: 56..57
<223> OTHER INFORMATION: (i) X5 means V and X6 means G or (ii) X5 means
      G and X6 means V

<400> SEQUENCE: 1

Arg Pro Ser Xaa Cys Asn Leu Pro Val Lys Pro Gly Pro Cys Xaa Gly
1               5                   10                  15

Phe Phe Ser Ala Phe Tyr Tyr Ser Gln Lys Xaa Asn Lys Cys His Ser
            20                  25                  30

Phe Thr Tyr Gly Gly Cys Ala Gly Asn Ala Asn Arg Phe Ser Thr Xaa
        35                  40                  45

Glu Lys Cys Arg Arg Thr Cys Xaa Xaa
    50                  55

<210> SEQ ID NO 2
<211> LENGTH: 57
<212> TYPE: PRT
<213> ORGANISM: Artificial Sequence
<223> OTHER INFORMATION: K39A
<220> FEATURE:
<223> OTHER INFORMATION: K39A

<400> SEQUENCE: 2

Arg Pro Ser Phe Cys Asn Leu Pro Val Lys Pro Gly Pro Cys Asn Gly
1               5                   10                  15

Phe Phe Ser Ala Phe Tyr Tyr Ser Gln Lys Thr Asn Lys Cys His Ser
            20                  25                  30

Phe Thr Tyr Gly Gly Cys Ala Gly Asn Ala Asn Arg Phe Ser Thr Ile
        35                  40                  45

Glu Lys Cys Arg Arg Thr Cys Val Gly
    50                  55

<210> SEQ ID NO 3
<211> LENGTH: 57
<212> TYPE: PRT
<213> ORGANISM: Artificial Sequence
<223> OTHER INFORMATION: K39A+I48L
<220> FEATURE:
<223> OTHER INFORMATION: K39A+I48L

<400> SEQUENCE: 3

Arg Pro Ser Phe Cys Asn Leu Pro Val Lys Pro Gly Pro Cys Asn Gly
1               5                   10                  15

Phe Phe Ser Ala Phe Tyr Tyr Ser Gln Lys Thr Asn Lys Cys His Ser
            20                  25                  30

Phe Thr Tyr Gly Gly Cys Ala Gly Asn Ala Asn Arg Phe Ser Thr Leu
        35                  40                  45

Glu Lys Cys Arg Arg Thr Cys Val Gly
    50                  55

<210> SEQ ID NO 4
<211> LENGTH: 57
<212> TYPE: PRT
<213> ORGANISM: Artificial Sequence
<223> OTHER INFORMATION: N15A+K39A+I48L
<220> FEATURE:
<223> OTHER INFORMATION: N15A+K39A+I48L

<400> SEQUENCE: 4

Arg Pro Ser Phe Cys Asn Leu Pro Val Lys Pro Gly Pro Cys Ala Gly
```

-continued

```
1                5                    10                    15

Phe Phe Ser Ala Phe Tyr Tyr Ser Gln Lys Thr Asn Lys Cys His Ser
            20                    25                    30

Phe Thr Tyr Gly Gly Cys Ala Gly Asn Ala Asn Arg Phe Ser Thr Leu
        35                    40                    45

Glu Lys Cys Arg Arg Thr Cys Val Gly
    50                    55
```

```
<210> SEQ ID NO 5
<211> LENGTH: 57
<212> TYPE: PRT
<213> ORGANISM: Artificial Sequence
<223> OTHER INFORMATION: F4G K39A T27D
<220> FEATURE:
<223> OTHER INFORMATION: F4G K39A T27D

<400> SEQUENCE: 5

Arg Pro Ser Gly Cys Asn Leu Pro Val Lys Pro Gly Pro Cys Asn Gly
1                5                    10                    15

Phe Phe Ser Ala Phe Tyr Tyr Ser Gln Lys Asp Asn Lys Cys His Ser
            20                    25                    30

Phe Thr Tyr Gly Gly Cys Ala Gly Asn Ala Asn Arg Phe Ser Thr Ile
        35                    40                    45

Glu Lys Cys Arg Arg Thr Cys Val Gly
    50                    55
```

```
<210> SEQ ID NO 6
<211> LENGTH: 57
<212> TYPE: PRT
<213> ORGANISM: Artificial Sequence
<223> OTHER INFORMATION: MQ-LEAD F4G+K39A+T27D+I48E
<220> FEATURE:
<223> OTHER INFORMATION: MQ-LEAD F4G+K39A+T27D+I48E

<400> SEQUENCE: 6

Arg Pro Ser Gly Cys Asn Leu Pro Val Lys Pro Gly Pro Cys Asn Gly
1                5                    10                    15

Phe Phe Ser Ala Phe Tyr Tyr Ser Gln Lys Asp Asn Lys Cys His Ser
            20                    25                    30

Phe Thr Tyr Gly Gly Cys Ala Gly Asn Ala Asn Arg Phe Ser Thr Glu
        35                    40                    45

Glu Lys Cys Arg Arg Thr Cys Val Gly
    50                    55
```

```
<210> SEQ ID NO 7
<211> LENGTH: 57
<212> TYPE: PRT
<213> ORGANISM: Artificial Sequence
<223> OTHER INFORMATION: WT MQ1 peptide
<220> FEATURE:
<223> OTHER INFORMATION: WT MQ1 peptide

<400> SEQUENCE: 7

Arg Pro Ser Phe Cys Asn Leu Pro Val Lys Pro Gly Pro Cys Asn Gly
1                5                    10                    15

Phe Phe Ser Ala Phe Tyr Tyr Ser Gln Lys Thr Asn Lys Cys His Ser
            20                    25                    30

Phe Thr Tyr Gly Gly Cys Lys Gly Asn Ala Asn Arg Phe Ser Thr Ile
        35                    40                    45

Glu Lys Cys Arg Arg Thr Cys Val Gly
    50                    55
```

```
<210> SEQ ID NO 8
<211> LENGTH: 57
<212> TYPE: PRT
<213> ORGANISM: Artificial Sequence
<223> OTHER INFORMATION: K10A
<220> FEATURE:
<223> OTHER INFORMATION: K10A

<400> SEQUENCE: 8

Arg Pro Ser Phe Cys Asn Leu Pro Val Ala Pro Gly Pro Cys Asn Gly
1               5                   10                  15

Phe Phe Ser Ala Phe Tyr Tyr Ser Gln Lys Thr Asn Lys Cys His Ser
            20                  25                  30

Phe Thr Tyr Gly Gly Cys Lys Gly Asn Ala Asn Arg Phe Ser Thr Leu
        35                  40                  45

Glu Lys Cys Arg Arg Thr Cys Val Gly
    50                  55

<210> SEQ ID NO 9
<211> LENGTH: 57
<212> TYPE: PRT
<213> ORGANISM: Artificial Sequence
<223> OTHER INFORMATION: K10E
<220> FEATURE:
<223> OTHER INFORMATION: K10E

<400> SEQUENCE: 9

Arg Pro Ser Phe Cys Asn Leu Pro Val Glu Pro Gly Pro Cys Asn Gly
1               5                   10                  15

Phe Phe Ser Ala Phe Tyr Tyr Ser Gln Lys Thr Asn Lys Cys His Ser
            20                  25                  30

Phe Thr Tyr Gly Gly Cys Lys Gly Asn Ala Asn Arg Phe Ser Thr Leu
        35                  40                  45

Glu Lys Cys Arg Arg Thr Cys Val Gly
    50                  55

<210> SEQ ID NO 10
<211> LENGTH: 57
<212> TYPE: PRT
<213> ORGANISM: Artificial Sequence
<223> OTHER INFORMATION: F17A
<220> FEATURE:
<223> OTHER INFORMATION: F17A

<400> SEQUENCE: 10

Arg Pro Ser Phe Cys Asn Leu Pro Val Lys Pro Gly Pro Cys Asn Gly
1               5                   10                  15

Ala Phe Ser Ala Phe Tyr Tyr Ser Gln Lys Thr Asn Lys Cys His Ser
            20                  25                  30

Phe Thr Tyr Gly Gly Cys Lys Gly Asn Ala Asn Arg Phe Ser Thr Leu
        35                  40                  45

Glu Lys Cys Arg Arg Thr Cys Val Gly
    50                  55

<210> SEQ ID NO 11
<211> LENGTH: 57
<212> TYPE: PRT
<213> ORGANISM: Artificial Sequence
<223> OTHER INFORMATION: F18A
<220> FEATURE:
<223> OTHER INFORMATION: F18A
```

-continued

```
<400> SEQUENCE: 11

Arg Pro Ser Phe Cys Asn Leu Pro Val Lys Pro Gly Pro Cys Asn Gly
1               5                   10                  15

Phe Ala Ser Ala Phe Tyr Tyr Ser Gln Lys Thr Asn Lys Cys His Ser
            20                  25                  30

Phe Thr Tyr Gly Gly Cys Lys Gly Asn Ala Asn Arg Phe Ser Thr Leu
        35                  40                  45

Glu Lys Cys Arg Arg Thr Cys Val Gly
    50                  55

<210> SEQ ID NO 12
<211> LENGTH: 57
<212> TYPE: PRT
<213> ORGANISM: Artificial Sequence
<223> OTHER INFORMATION: N41A
<220> FEATURE:
<223> OTHER INFORMATION: N41A

<400> SEQUENCE: 12

Arg Pro Ser Phe Cys Asn Leu Pro Val Lys Pro Gly Pro Cys Asn Gly
1               5                   10                  15

Phe Phe Ser Ala Phe Tyr Tyr Ser Gln Lys Thr Asn Lys Cys His Ser
            20                  25                  30

Phe Thr Tyr Gly Gly Cys Lys Gly Ala Ala Asn Arg Phe Ser Thr Ile
        35                  40                  45

Glu Lys Cys Arg Arg Thr Cys Val Gly
    50                  55

<210> SEQ ID NO 13
<211> LENGTH: 57
<212> TYPE: PRT
<213> ORGANISM: Artificial Sequence
<223> OTHER INFORMATION: R44A
<220> FEATURE:
<223> OTHER INFORMATION: R44A

<400> SEQUENCE: 13

Arg Pro Ser Phe Cys Asn Leu Pro Val Lys Pro Gly Pro Cys Asn Gly
1               5                   10                  15

Phe Phe Ser Ala Phe Tyr Tyr Ser Gln Lys Thr Asn Lys Cys His Ser
            20                  25                  30

Phe Thr Tyr Gly Gly Cys Lys Gly Asn Ala Asn Ala Phe Ser Thr Leu
        35                  40                  45

Glu Lys Cys Arg Arg Thr Cys Val Gly
    50                  55

<210> SEQ ID NO 14
<211> LENGTH: 57
<212> TYPE: PRT
<213> ORGANISM: Artificial Sequence
<223> OTHER INFORMATION: R44E
<220> FEATURE:
<223> OTHER INFORMATION: R44E

<400> SEQUENCE: 14

Arg Pro Ser Phe Cys Asn Leu Pro Val Lys Pro Gly Pro Cys Asn Gly
1               5                   10                  15

Phe Phe Ser Ala Phe Tyr Tyr Ser Gln Lys Thr Asn Lys Cys His Ser
            20                  25                  30

Phe Thr Tyr Gly Gly Cys Lys Gly Asn Ala Asn Glu Phe Ser Thr Leu
        35                  40                  45
```

-continued

```
Glu Lys Cys Arg Arg Thr Cys Val Gly
    50                  55

<210> SEQ ID NO 15
<211> LENGTH: 9
<212> TYPE: PRT
<213> ORGANISM: Artificial Sequence
<223> OTHER INFORMATION: Enzyme substrate
<220> FEATURE:
<221> NAME/KEY: CHAIN
<222> LOCATION: 1
<223> OTHER INFORMATION: (7-Methoxycoumarin-4-yl) acetyl
<220> FEATURE:
<223> OTHER INFORMATION: Enzyme substrate
<220> FEATURE:
<221> NAME/KEY: CHAIN
<222> LOCATION: 9
<223> OTHER INFORMATION: 2, 4-Dinitrophenyl

<400> SEQUENCE: 15

Arg Pro Pro Gly Phe Ser Ala Phe Lys
1               5

<210> SEQ ID NO 16
<211> LENGTH: 7
<212> TYPE: PRT
<213> ORGANISM: Artificial Sequence
<223> OTHER INFORMATION: Enzyme substrate
<220> FEATURE:
<221> NAME/KEY: CHAIN
<222> LOCATION: 1
<223> OTHER INFORMATION: (7-Methoxycoumarin-4-yl) acetyl
<220> FEATURE:
<223> OTHER INFORMATION: Enzyme substrate
<220> FEATURE:
<221> NAME/KEY: CHAIN
<222> LOCATION: 7
<223> OTHER INFORMATION: 2, 4-Dinitrophenyl

<400> SEQUENCE: 16

Tyr Val Ala Asp Ala Pro Lys
1               5

<210> SEQ ID NO 17
<211> LENGTH: 12
<212> TYPE: PRT
<213> ORGANISM: Artificial Sequence
<223> OTHER INFORMATION: Enzyme substrate
<220> FEATURE:
<221> NAME/KEY: CHAIN
<222> LOCATION: 1
<223> OTHER INFORMATION: (7-Methoxycoumarin-4-yl) acetyl
<220> FEATURE:
<223> OTHER INFORMATION: Enzyme substrate
<220> FEATURE:
<221> NAME/KEY: NON_STD
<222> LOCATION: 7
<223> OTHER INFORMATION: X is N-3-(2,4-dinitrophenyl)-L-alpha,beta-
      diaminopropionyl]

<400> SEQUENCE: 17

Pro Leu Ala Gln Ala Val Xaa Arg Ser Ser Ser Arg
1               5                   10

<210> SEQ ID NO 18
<211> LENGTH: 13
<212> TYPE: PRT
<213> ORGANISM: Artificial Sequence
<223> OTHER INFORMATION: Enzyme substrate
<220> FEATURE:
<221> NAME/KEY: CHAIN
```

```
<222> LOCATION: 1
<223> OTHER INFORMATION: (7-Methoxycoumarin-4-yl) acetyl
<220> FEATURE:
<223> OTHER INFORMATION: Enzyme substrate
<220> FEATURE:
<221> NAME/KEY: CHAIN
<222> LOCATION: 11
<223> OTHER INFORMATION: 2, 4-Dinitrophenyl

<400> SEQUENCE: 18

Ser Glu Val Asn Leu Asp Ala Glu Phe Arg Lys Arg Arg
1               5                   10

<210> SEQ ID NO 19
<211> LENGTH: 4
<212> TYPE: PRT
<213> ORGANISM: Artificial Sequence
<223> OTHER INFORMATION: Enzyme substrate
<220> FEATURE:
<221> NAME/KEY: MOD_RES
<222> LOCATION: 1
<223> OTHER INFORMATION: Acetyl ACETYLATION
<220> FEATURE:
<223> OTHER INFORMATION: Enzyme substrate
<220> FEATURE:
<221> NAME/KEY: CHAIN
<222> LOCATION: 4
<223> OTHER INFORMATION: 7-amino-4-methyl coumarin

<400> SEQUENCE: 19

Leu Glu His Asp
1

<210> SEQ ID NO 20
<211> LENGTH: 4
<212> TYPE: PRT
<213> ORGANISM: Artificial Sequence
<223> OTHER INFORMATION: Enzyme substrate
<220> FEATURE:
<221> NAME/KEY: MOD_RES
<222> LOCATION: 1
<223> OTHER INFORMATION: Acetyl ACETYLATION
<220> FEATURE:
<223> OTHER INFORMATION: Enzyme substrate
<220> FEATURE:
<221> NAME/KEY: CHAIN
<222> LOCATION: 4
<223> OTHER INFORMATION: 7-amino-4-methyl coumarin

<400> SEQUENCE: 20

Asp Glu Val Asp
1

<210> SEQ ID NO 21
<211> LENGTH: 4
<212> TYPE: PRT
<213> ORGANISM: Artificial Sequence
<223> OTHER INFORMATION: Enzyme substrate
<220> FEATURE:
<221> NAME/KEY: MOD_RES
<222> LOCATION: 1
<223> OTHER INFORMATION: Acetyl ACETYLATION
<220> FEATURE:
<223> OTHER INFORMATION: Enzyme substrate
<220> FEATURE:
<221> NAME/KEY: CHAIN
<222> LOCATION: 4
<223> OTHER INFORMATION: 7-amino-4-methyl coumarin

<400> SEQUENCE: 21

Trp Glu His Asp
1
```

```
<210> SEQ ID NO 22
<211> LENGTH: 7
<212> TYPE: PRT
<213> ORGANISM: Artificial Sequence
<223> OTHER INFORMATION: Enzyme substrate
<220> FEATURE:
<221> NAME/KEY: CHAIN
<222> LOCATION: 1
<223> OTHER INFORMATION: (7-Methoxycoumarin-4-yl) acetyl
<220> FEATURE:
<223> OTHER INFORMATION: Enzyme substrate
<220> FEATURE:
<221> NAME/KEY: NON_STD
<222> LOCATION: 5
<223> OTHER INFORMATION: N-3-(2,4-dinitrophenyl)-L-alpha,beta-
      diaminopropionyl] linked to 2, 4-Dinitrophenyl

<400> SEQUENCE: 22

Pro Leu Gly Leu Xaa Ala Arg
1               5

<210> SEQ ID NO 23
<211> LENGTH: 4
<212> TYPE: PRT
<213> ORGANISM: Artificial Sequence
<223> OTHER INFORMATION: Enzyme substrate
<220> FEATURE:
<221> NAME/KEY: NON_STD
<222> LOCATION: 1
<223> OTHER INFORMATION: Succinyl
<220> FEATURE:
<223> OTHER INFORMATION: Enzyme substrate
<220> FEATURE:
<221> NAME/KEY: CHAIN
<222> LOCATION: 4
<223> OTHER INFORMATION: 7-amino-4-methyl coumarin

<400> SEQUENCE: 23

Ala Ala Pro Phe
1

<210> SEQ ID NO 24
<211> LENGTH: 4
<212> TYPE: PRT
<213> ORGANISM: Artificial Sequence
<223> OTHER INFORMATION: Enzyme substrate
<220> FEATURE:
<221> NAME/KEY: NON_STD
<222> LOCATION: 1
<223> OTHER INFORMATION: Methoxysuccinyl
<220> FEATURE:
<223> OTHER INFORMATION: Enzyme substrate
<220> FEATURE:
<221> NAME/KEY: CHAIN
<222> LOCATION: 4
<223> OTHER INFORMATION: 7-amino-4-methyl coumarin

<400> SEQUENCE: 24

Ala Ala Pro Val
1

<210> SEQ ID NO 25
<211> LENGTH: 10
<212> TYPE: PRT
<213> ORGANISM: Artificial Sequence
<223> OTHER INFORMATION: Enzyme substrate
<220> FEATURE:
<221> NAME/KEY: CHAIN
<222> LOCATION: 1
<223> OTHER INFORMATION: (7-Methoxycoumarin-4-yl) acetyl
<220> FEATURE:
```

-continued

```
<223> OTHER INFORMATION: Enzyme substrate
<220> FEATURE:
<221> NAME/KEY: NON_STD
<222> LOCATION: 7
<223> OTHER INFORMATION: X is Norvaline
<220> FEATURE:
<221> NAME/KEY: CHAIN
<222> LOCATION: 10
<223> OTHER INFORMATION: 2, 4-Dinitrophenyl

<400> SEQUENCE: 25

Arg Pro Lys Pro Val Glu Xaa Trp Arg Lys
1               5                   10
```

VASOPRESSIN-2 RECEPTOR ANTAGONIST PEPTIDES AND USES THEREOF

CROSS-REFERENCE TO RELATED APPLICATIONS

The present application is the national stage of international application PCT/EP2021/067248, filed on Jun. 23, 2021, and claims the benefit of the filing date of European Appl. No. 20305696.5, filed on Jun. 24, 2020.

FIELD OF THE DISCLOSURE

The present disclosure concerns the medical field relating to the treatment of diseases involving vasopressin-2 receptor.

BACKGROUND OF THE DISCLOSURE

The type 2 vasopressin receptor (V2R) is a G-protein-coupled receptor encoded by the AVPR2 gene located on chromosome Xq28. V2R belongs to the vasopressin hormone sensitive receptor family as the V1a, the V1b and the oxytocin receptors. V2R, as many GPCRs, induces a pleiotropic action through both G protein-dependent and G protein-independent mechanisms.

V2R is notably expressed in the distal part of the nephron. Once activated in the collecting duct, the V2R/Gas pathway stimulates intracellular cAMP production, which activates the protein kinase A to phosphorylate the aquaporin-2, allowing its translocation from intracellular vesicles to the apical membrane via an intracellular calcium-dependent exocytosis mechanism. Further, water can go through aquaporin 2 at the apical membrane from the urine to the main cell before reaching the blood thanks to aquaporin 3 and aquaporin 4 at the basolateral membrane. Poorly recycled, V2R is associated with long-term activation thanks to an active complex AVP-V2R-beta-arrestin. A third V2 pathway led to the activation of ERK1/2 through the metalloprotei-nase-mediated activating the insulin-like growth factor receptor.

Both loss- and gain-of-function variants of V2R are associated with human diseases. Default in arginine-vasopressin (AVP) secretion is associated with hyponatremia with plasma sodium levels below 135 mmol/l in humans. It is associated with a number of diseases, including chronic heart failure, liver failure and chronic kidney disease, where it has been shown to be related with an increased risk of death. Ectopic AVP secretion in lung or prostate cancers can also lead to excessive circulating AVP levels, that can lead to hyponatremia. Also, V2R is also the therapeutic target for the Autosomal Dominant form of the Polycystic Kidney Disease (ADPKD). Many therapeutic strategies are developed for V2R-linked diseases, including ADPKD, but only the blockade of the V2R demonstrated its efficacy in human (Nagao et al., 2012, Exp Anim, Vol. 61: 477-488).

Outside the kidney, endothelial cells express the V2R where it participates in the control of the Von Willebrand factor expression. In the inner ear, V2R participates to the lymphatic sac volume regulation and is supposed to play a role in the Meniere disease (Eckhard et al., 2012, Mol Aspects Med, Vol. 33: 612-637). In bone, V2R may contribute to homeostasis (Tamma et al., 2013, Proc Natl Acad Sci USA, Vol. 110 (46): 18644-18649). Neuropeptides like AVP can be overexpressed in neuroendocrine tumors. Also, V2R is present ectopically in human lung, breast, pancreatic, colorectal and gastrointestinal tumors (Pifano et al., 2017, Front Oncol, Vol. 7—Article 11: 1-11).

Then, default in V2R activity is associated with a number of diseases, especially in human. However, despite the crucial physiological and pathological importance of V2R, the therapeutic arsenal for this receptor is poor. Only one antagonist molecule is principally used in the art, named tolvaptan, which is a benzazepine-derived molecule belonging to the family of vaptans, acting as an antagonist on the V2R with high affinity but with moderate selectivity versus the three other vasopressin-sensitive receptors. Tolvaptan is presently used for treatment of hyponatremia and ADPKD, but with many concerns due to its hepatotoxicity.

The excess secretion of AVP is a key etiologic factor for diseases such as hyponatremia and explains why the use of V2R antagonists is so efficient in pathological conditions characterized by euvolemic or hypervolemic hyponatremia, such as SIADH (Syndrome of Inappropriate AntiDiuretic Hormone secretion), hepatic cirrhosis and congestive heart failure (G I F; Ghali et ah, Cardiology, 2008, 111, 147-157).

The Congenital Nephrogenic Diabetes Insipidus is associated with inactivating mutations of the V2R. This leads to polyuria with severe dehydration in particular in children. The V2R antagonists (vaptans) behave as pharmacochaper-ones, they are able to penetrate the cell and can rescue the mutant receptors (Morello et al, J. Clin. Investigation, 2000, 105, 887-895).

By interacting with arrestin V2R stimulation leads to the activation of signaling pathways involving cAMP and MAP kinase thus favoring a proliferative response. For example, AVP injection in the rat induces the proliferation of renal tubular epithelial cells that can be inhibited by V2R antagonists (Alonso et al, Endocrinology, 2009, 150, 239-250). Moreover, diuretics such as V2R antagonists were able to inhibit the proliferation of renal cancer cells (Bolignano et al, Urol. Oncol., 2010, 28, 642-647) and of pulmonary cancer cells (Pequeux et al., Endocr. Relat. Cancer, 2004, 11, 871-885). These results indicate that V2R antagonists are good therapeutic candidates against different types of cancer.

The Von Willebrand factor (VWF) is implicated in primary hemostasis. It has been demonstrated that AVP and also the V2R specific agonist, dDAVP (Minirin®), increases VWF and factor VIII levels via their interaction with V2R (Kaufmann el al., J. Clin. Invest., 2000, 106, 107-116). An excess in coagulation can lead to thrombosis (clots) which could be cured by the use of V2R antagonists thus limiting the secretion of coagulation factors.

The V2R antagonist tolvaptan has also been used for treating cirrhosis. A previous meta-analysis showed that treatment with vaptans increased the risk of total adverse events in cirrhosis patients, due to its well-known hepatotoxicity. (Impact of Vaptans on Clinical Outcomes in Cirrhosis Patients: A Meta-Analysis of Randomized Controlled Trials, 2019, Frontiers in Pharmacology).

The V2R antagonist tolvaptan has further been used for treating heart failure. The effectiveness and safety of tolvaptan in real-world clinical settings was confirmed in this large-scale analysis. (Tolerability of Tolvaptan in Patients With Heart Failure—Final Results of the Samsca Post-Marketing Surveillance in Heart Failure (SMILE) Study, 2019, Circulation Journal).

Although vaptans have clearly proven the therapeutic effect of V2R antagonists on various pathologies, their therapeutic use is limited by some major drawbacks:

Vaptans and their metabolites are hepatotoxic. For this reason, their use necessitates a tight monitoring of the patients and their long-term administration is limited. Some of them are only injected intravenously which restrict their use to hospitalized patients.

Vaptans have some selectivity only for V2R with V2/Vla selectivity index which varies from 112 (Satavaptan) to 0.15 (Conivaptan).

Vaptans are antagonists for MAP kinase activation. Therefore, they are unable to block completely specific V2R-associated signaling pathways. Vaptans are poorly soluble in physiological buffers and have limited bioavailability (Bernier et al. JASN, 2006, 17, 591).

The most selective V2R antagonist known in the art is a peptide initially isolated from the mamba snake venom, which was named mambaquaretin (MQ1). MQ1 is a peptide of 57 amino acid residues in length which is reticulated by three disulfide bonds adopting the Kunitz peptide structure (Ciolek et al., 2017, Proc Natl Acad Sic USA, Vol. 114 (27): 7154-7159). The MQ1 peptide displays high affinity for the human V2R and no affinity at µM concentrations for 156 other GPCRs, including for V1aR, V1bR and OTR. The MQ1 peptide is a full competitive 30 antagonist for the three pathways linked to the Gas protein, the interaction with beta-arrestin and activation of MAP kinase (Ciolek et al., 2017, Proc Natl Acad Sic USA, Vol. 114 (27): 7154-7159). When administered, the MQ1 peptide induces a pure aquaretic effect, i.e. induces a loss of water without any loss of electrolytes. MQ1 efficacy in cystic kidney diseases was shown (Ciolek et al., 2017, Proc Natl Acad Sic USA, Vol. 114 (27): 7154-7159).

There is still a need for V2R antagonists, which are alternative or improved as compared with already known V2R antagonists, notably for medical purpose.

SUMMARY OF THE DISCLOSURE

The present disclosure relates to a peptide comprising a sequence having 80% or more amino acid identity with the amino acid sequence of SEQ ID NO. 1 below:

RPSX$_1$CNLPVKPGPCX$_2$GFFSAFYYSQKX$_3$NKCHSFTYGGCAGNANRFST

X$_4$EKCRRTCX$_5$X$_6$ wherein,

X1 means the amino acid residue F or G,
X2 means any amino acid residue, excepted a basic amino acid residue,
X3 means the amino acid residue T or D,
X4 means the amino acid residue I, L or E,
(i) X5 means V and X6 means G or (ii) X5 means G and X6 means V, and
the amino acid located at position 39 is A.

In some embodiments of the said peptide, X1 means the amino acid residue G.

In some embodiments of the said peptide, X2 means an amino acid residue selected in the group consisting of A, D, E, F, G, I, L, N, M, Q, S, T, V and Y.

In some embodiments of the said peptide, X3 means the amino acid residue D.

In some embodiments of the said peptide, X4 means the amino acid residue E or L.

In some embodiments, the said peptide comprises the amino acid sequence of SEQ ID NO. 1.

In some embodiments, the said peptide has 80% or more amino acid identity with a peptide selected in a group comprising SEQ ID NO. 2, SEQ ID NO. 3, SEQ ID NO. 4, SEQ ID NO. 5 and SEQ ID NO. 6. In some embodiments, the said peptide comprises an amino acid sequence selected in a group comprising SEQ ID NO. 2, SEQ ID NO. 3, SEQ ID NO. 4, SEQ ID NO. 5 and SEQ ID NO. 6. In some embodiments, the said peptide consists of an amino acid sequence selected in a group comprising SEQ ID NO. 2, SEQ ID NO. 3, SEQ ID NO. 4, SEQ ID NO. 5 and SEQ ID NO. 6.

The said peptide may be labeled with a detectable molecule.

This disclosure also relates to a nucleic acid encoding a peptide described above, which nucleic acid may be comprised in an expression vector.

This disclosure further pertains to a pharmaceutical composition comprising a peptide as defined above and a physiologically acceptable carrier.

This disclosure also concerns a peptide as described above, for its use as a medicament. It also pertains to the said peptide for use for treating a disease selected in the group consisting of pathologic conditions characterized by euvolemic or hypovolemic hyponatremia, Nephrogenic Syndrome of Inappropriate Antidiuresis, Congenital Nephrogenic Diabetes Insipidus, Polycystic kidney disease, cancers, thrombosis, Meniere disease, refractory liver disease and heart failure.

This disclosure also relates to the in vitro use of a labeled peptide as described above for detecting cells expressing vasopressin-2 receptor.

It further pertains to an in vitro method for detecting a dysregulation of vasopressin-2 receptor cell expression comprising the steps of:

a) providing cells to be tested,
b) bringing the cells provided at step a) with a labeled peptide according to claim 11,
c) measuring the expression level value of vasopressin-2 receptor cell expression,
d) comparing the expression level value obtained at step c) with a reference expression level value,
e) determining the occurrence of a dysregulation of vasopressing-2 receptor cell expression.

It also concerns a diagnostic reagent comprising a labeled peptide as described above.

The sequences of the two peptides have been entered into the NETMHCNETMHCPAN 3.2 software <www.IEDB.org>, By selecting HLA-DR molecules among the most frequent in the European and North American population.

NETMHC software allows predicting the possible association of the sequences with HLA class II molecules. The selected class II HLA molecules are among the most frequent in the European and North American population. The predicted score is a percentile which is reported for each sequence of 9 amino acids on the first amino acid. The lower the score, the stronger the association of the sequence with the HLA class II molecule is expected to be.

Figure 1:
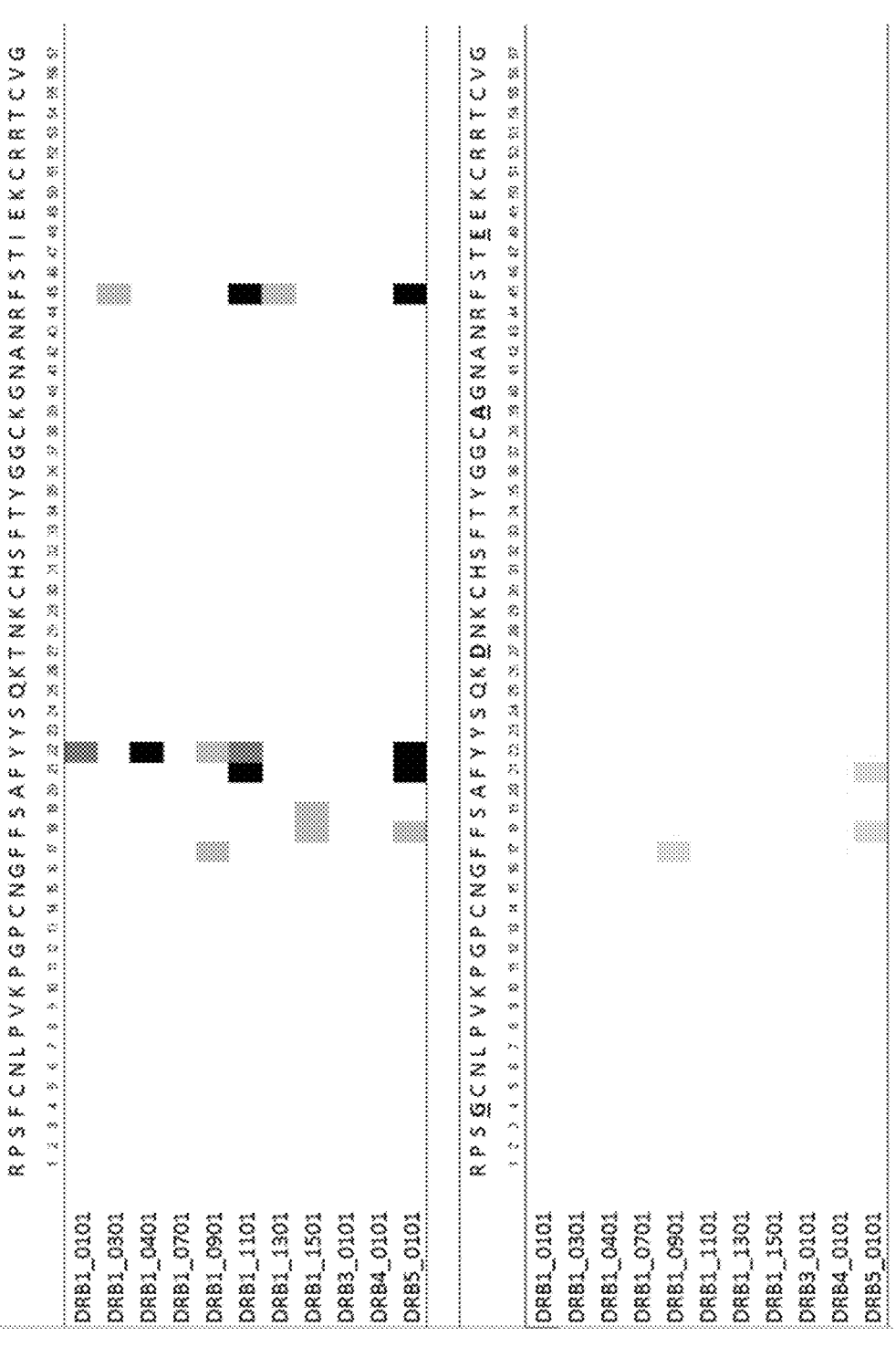
FIG. 1 illustrates in silico prediction of the immunogenicity of the known MQ1 V2R antagonist peptide of SEQ ID NO.7 (which may also be termed "U-Da2a) and a V2R antagonist termed MQ-LEAD according to the disclosure of SEQ ID NO. 6, respectively.

In FIG. 1, each numbered row corresponds to an amino acid residue of each of the 57 amino acid residues long peptide. Upper panel: the known MQ1 V2R antagonist peptide. Lower panel: the MQ-LEAD peptide of SEQ ID NO. 6). In the lines named "DRBx_nnnn", DRBx is the name of the HLA-DRB locus and nnnn the number of the allele.

Immunogenicity scores: (i) Score below 10% (black), (ii) between 10 and 20% (dark grey) and (iii) between 20% and 30% (light grey). Bold and underlined positions in the lower panel consist of the differences in amino acid residues in the MQ-LEAD peptide as compared with the MQ1 peptide.

Figure 2:
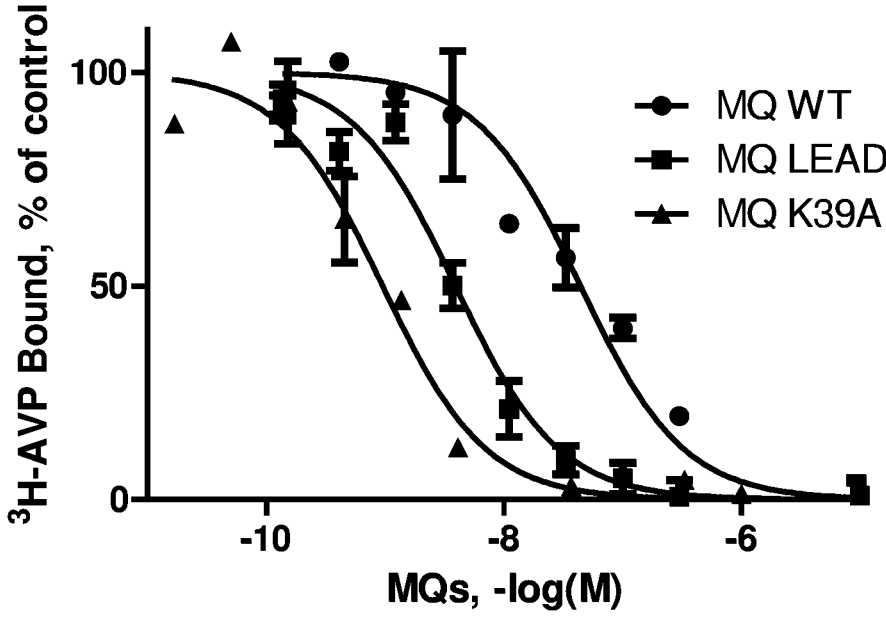

FIG. 2 illustrates the binding of V2R antagonist peptides according to the disclosure to V2R, as compared with the V2R binding property of the known MQ1 peptide. Abscissa: log of Molar concentration of the tested V2R antagonist peptides or MQ1 peptides. Ordinate: 3H-AVP Bound, % of control FIG. 3 illustrates the effects of V2R antagonist peptides on diuresis. The tested V2R antagonist peptides were injected i.p. in rat (SprageDelay) at 3 nmol/kg each day (arrows) and diuresis was followed over time.

Figure 3A:
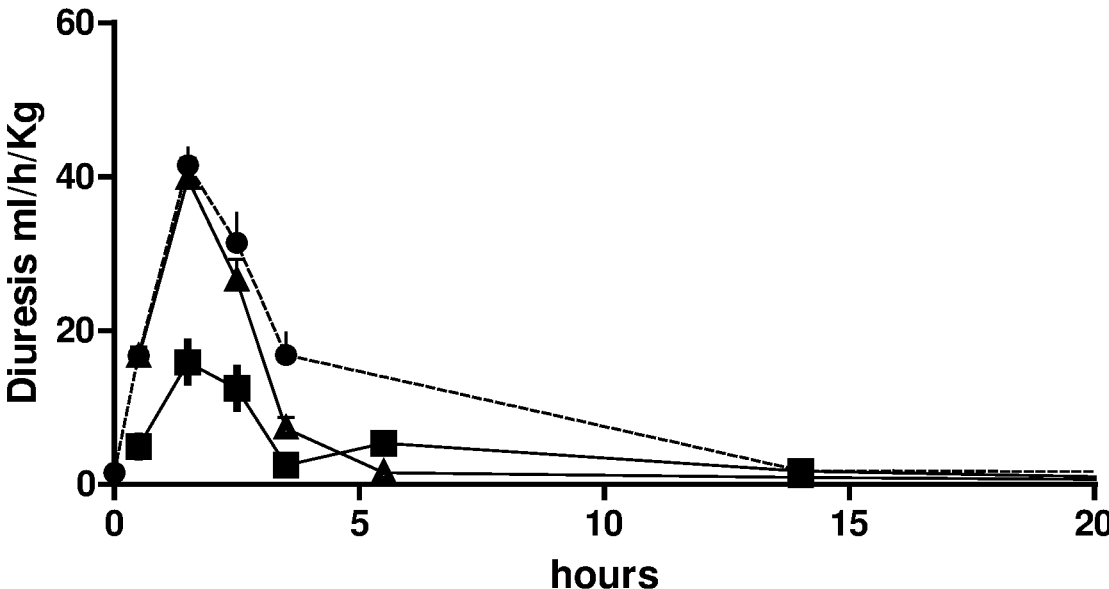

FIG. 3A. Abscissa: Time period, as expressed in hours. Ordinate: diuresis, as expressed in ml/h/kg. Tested conditions; (i) MQ1 peptide [black circle "●", dashed line], (ii) MQ-LEAD [black square "□", continuous line] and (iii) MQ K39A [black triangle "▲", continuous line].

Figure 3B:
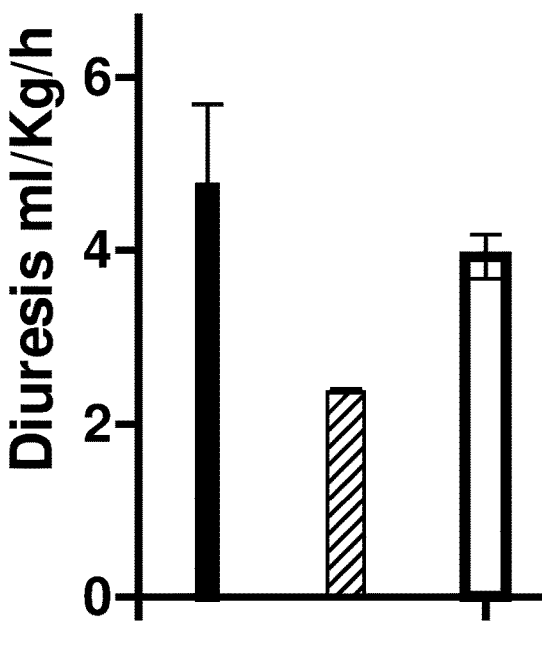

FIG. 3B. Abscissa: from the left to the right: (i) MQ-LEAD [Black bar], (ii) MQ1 peptide [dashed bar] and (iii) MQ K39A [empty bar].

Figure 4:
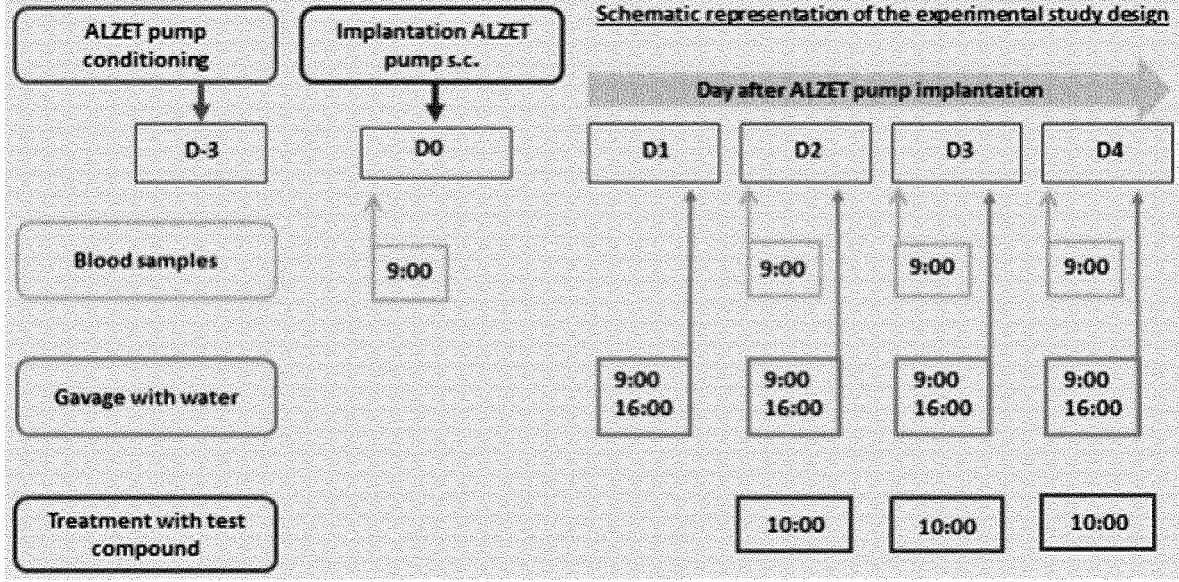

FIG. 4 illustrates a schematic representation of the experimental study design.

Figure 5:
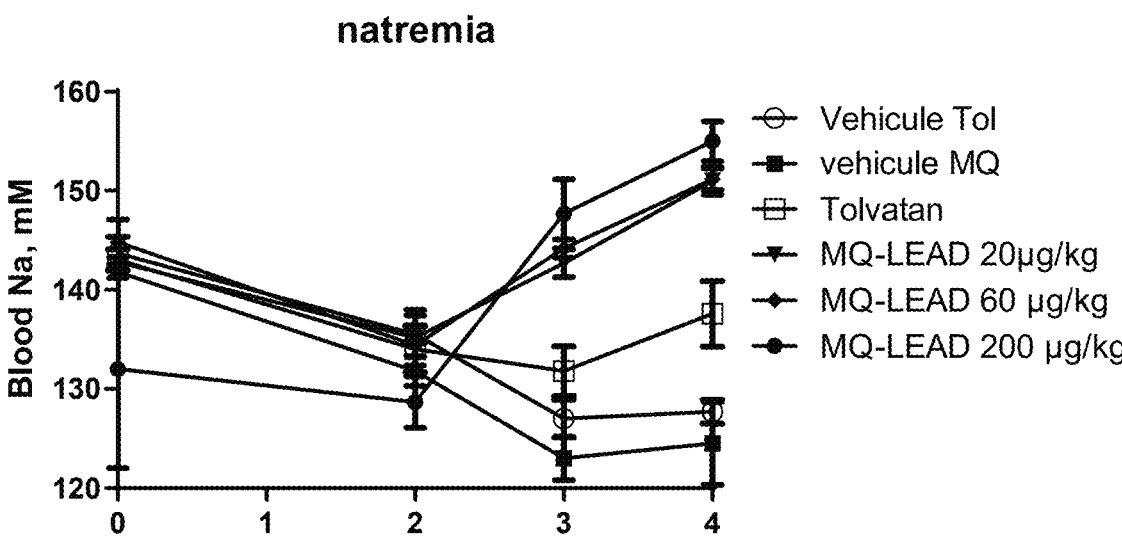

FIG. 5 illustrates the effects of MQ-LEAD at 3 doses, tolvaptan at 1 dose and their vehicles on natremia on days 0-2-3-4 in male rats implanted with DDAVP on day 0.

Abscissa: time period, as expressed in days. Ordinate: blood Na+ concentration, as expressed in mM. Tested conditions: (i) open circle ">": vehicle for tolvaptan, 1% HPMC in distilled water, (ii) black square "■": vehicle for the V2R antagonist peptide MQ-LEAD, physiological saline, (iii) open square "□": tolvaptan, (iv) reverse triangle "▽": MQ-LEAD at 20 μg/kg, (v) diamond "●": MQ-LEAD at 60 μg/kg and (vi) closed circle "•": MQ-LEAD at 200 μg/kg.

Figure 6:
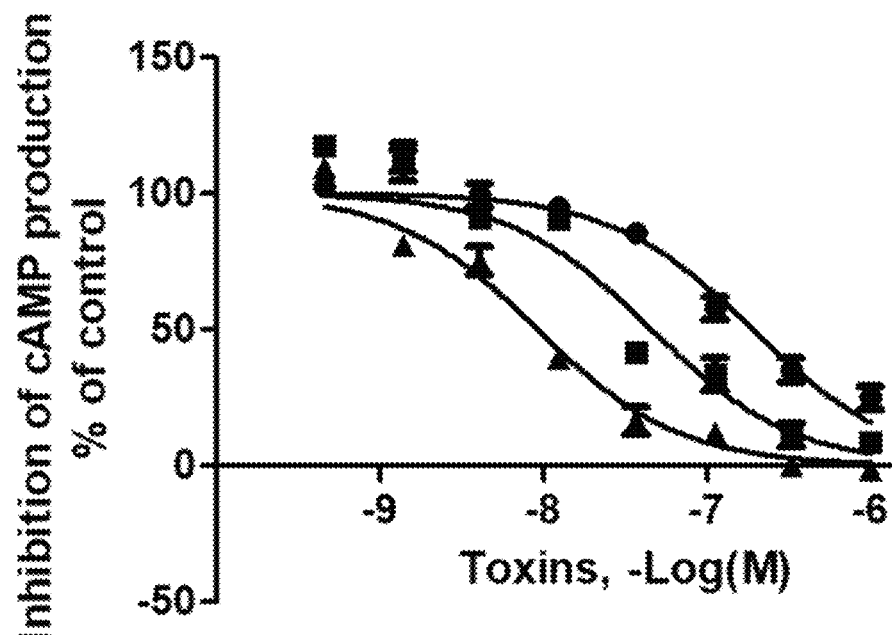

FIG. 6 illustrates inhibition of cAMP production by V2R antagonist peptides. Abscissa: concentration of peptide, as expressed in −Log(M). Ordinate: inhibition of cAMP production, as expressed as percent of control. (i) Circle "●": MQ1 peptide; (ii) square "■": MQ K39A peptide; (iii) triangle "▲": MQ-LEAD peptide.

DETAILED DESCRIPTION OF THE DISCLOSURE

Definitions

The term "subject" refers to any single subject for which therapy is desired or that is participating in a clinical trial, epidemiological study or used as a control, including humans and mammalian veterinary patients such as cattle, horses, dogs and cats. In certain preferred embodiments, the subject is a human.

The term "treat" or "treating" a cancer as used herein means to administer a combination therapy according to the present invention to a subject having a cancer.

The term "pharmaceutically acceptable" means what is useful in preparing a pharmaceutical composition generally safe, non-toxic, and neither biologically nor otherwise undesirable and includes what is acceptable for veterinary as well as human pharmaceutical use.

Within the scope of the present invention, the "percentage identity" between two sequences of nucleic acids or peptides/proteins means the percentage of identical nucleotides or amino acid residues between the two sequences to be compared, obtained after optimal alignment, this percentage being purely statistical and the differences between the two sequences being distributed randomly along their length. The comparison of sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981), by means of the local homology algorithm of Neddleman and Wunsch (1970), by means of the similarity search method of Pearson and Lipman (1988) or by means of computer software using these algorithms (GAP, BESTFIT, FASTA and TFASTA in the Wisconsin Genetics Software Package, Genetics Computer Group, 575 Science Dr., Madison, WI, or by the comparison software BLAST NR or BLAST P).

The percentage identity between two sequences is determined by comparing the two optimally-aligned sequences in which the sequence to compare can have additions or deletions compared to the reference sequence for optimal alignment between the two sequences. Percentage identity is calculated by determining the number of positions at which the nucleotide or amino acid residue is identical between the two sequences, preferably between the two complete sequences, dividing the number of identical positions by the total number of positions in the alignment window and multiplying the result by 100 to obtain the percentage identity between the two sequences.

As used herein, "V2R antagonist activity" relates to the activity of a substance, such as the activity of a peptide, to (i) bind to a V2R, most preferably a human V2R, with a binding affinity value of less than 100 nM and (ii) inhibit cAMP production with an IC50 value of less than 1000 nM.

DETAILED DISCLOSURE

The present disclosure relates to a family of vasopressin-2 receptor antagonists that may be mainly used for medical and diagnostic purposes.

The inventors have identified a family of peptides, sharing specific structural features, that behave as highly potent vasopressin-2 antagonists, both in vitro and in vivo. These peptides are derived from the known MQ1 peptide (also termed "U-Da2a") described in the PCT application published under WO 2014/041526.

The inventors have found that a plurality of MQ1-derived peptides, having as the common feature the presence of a Lysine (K) residue at the amino acid position 39, inhibit the activity of the human vasopressin-2 receptor (also termed "V2R" herein) at the nanomolar level. Noticeably, the said family of peptides that are disclosed possesses a significantly higher V2R inhibition capacity than that of the known MQ1 peptide. These peptides have an affinity for V2R which is several times higher than the known MQ1 peptide, such as eight times higher affinity for V2R as compared to the known MQ1 peptide.

These peptides disclosed herein behave as strong antagonist compounds of the vasopressin-2 receptor and will then be collectively termed "V2R antagonist peptides" herein.

As shown in the examples, the V2R antagonist peptides disclosed herein strongly inhibit cAMP production by V2R-expressing cells under vasopressin activation, at a much lower concentration than the known MQ1 peptide.

In vivo, the V2R antagonist peptides of the present disclosure actually induce an aquaretic effect. Noticeably, the V2R antagonist peptides disclosed herein are about 500 times more potent than tolvaptan, the most therapeutically used V2R antagonist compound, for treating hyponatremia, i.e. are about 500 times more potent than the major V2R antagonist compound that is actually used in such a physiological context, to date.

V2R Antagonist Peptides

The present disclosure relates to a peptide comprising a sequence having 80% or more amino acid identity with the amino acid sequence of SEQ ID NO. 1 below:

RPSX$_1$CNLPVKPGPCX$_2$GFFSAFYYSQKX$_3$NKCHSFTYGGCAGNANRFST

X$_4$EKCRRTCX$_5$X$_6$ wherein,

X1 means the amino acid residue F or G,

X2 means any amino acid residue, excepted a basic amino acid residue,

X3 means the amino acid residue T or D,

X4 means the amino acid residue I, L or E, (i) X5 means V and X6 means G or (ii) X5 means G and X6 means V, and the amino acid located at position 39 is A.

As used herein, "X$_n$" and "Xn" may be indifferently used for meaning the same variable amino acid residue.

As used herein, amino acid residues may be selected in the group consisting of Alanine (A), Arginine R, Asparagine (N), Aspartic acid (D), Cysteine (C), Glutamic acid (E), Glutamine (Q), Glycine (G), Histidine (H), Isoleucine (I), Leucine (L), Lysine (K), methionine (M), phenylalanine (F), Proline (P), Serine (S), Threonine (T), Tryptophan (W), Tyrosine (Y) and Valine (V) as well as amino acid analogs including D-amino acids, beta alanine, gamma-aminobutyric acid, delta-aminolevulinic acid, 4-aminobenzoic acid, aminoisobutyric acid, dehydroalanine, cystine, cystathionine, lanthionine, djenkolic acid, diaminopimelic acid, norleucine, alloisoleucine, isoserine, N-ethyl glycine, N-propyl glycine, N-isopropyl glycine, N-methyl alanine, N-ethyl alanine, and isoserine.

However, amino acid residues are most preferably selected in the group consisting of the 20 conventional amino acid residues.

All amino acids in the peptides of the invention can be in both D- or L-form, although the naturally occurring L-form is preferred.

Without wishing to be bound by any particular theory, the inventors believe that there is a direct relationship between the high V2R antagonist properties of the peptides disclosed herein and the presence of an alanine residue (A) at the amino acid position 39 of SEQ ID NO. 1.

As shown in the examples herein, the V2R antagonist peptides disclosed herein are also expected to be endowed with a reduced immunogenicity. The reduced immunogenicity of these peptides allows qualifying them for being used for treating various pathologic conditions linked to a V2R dysfunction, especially those requiring their repeated administration to a subject, such as, illustratively, Nephrogenic Syndrome of Inappropriate diuresis or congenital Nephrogenic Diabetes Insipidus.

Further, without wishing to be bound by any particular theory, the inventors believe that the V2R antagonist peptides according to the present disclosure are highly selective for V2R, as it has been shown for the known MQ1 peptide. Indeed, a high selectivity of the V2R antagonist peptides for V2R means that low undesirable effects are to be expected when administered for therapeutic purposes, in contrast, for example, to the largely used V2R antagonist tolvaptan for which a number of undesirable effects have been reported due to its moderate selectivity for V2R.

The inventors believe that the affinity of a V2R antagonist peptide disclosed herein is not substantially affected by the identity of the amino acid residue X2, excepted if the amino acid residue X2 consists of a basic amino acid residue. In contrast, the presence of a basic amino acid residue as the amino acid residue X2 negatively affect the affinity of the peptide for the V2R, causing an alteration of its capacity of binding to V2R.

As used herein, including for the amino acid residue X2, a basic amino acid residue consists of an amino acid residue, either being a conventional or an unconventional amino acid residue, that is positively charged at pH 7.0. Basic conventional amino acid residues are selected in the group consisting of K (Lysine), R (Arginine) and H (Histidine).

Thus, in preferred embodiments, X2 means any amino acid residue excepted K, R and H.

In preferred embodiments, X2 means an amino acid residue selected in the group consisting of A, D, E, F, G, I, L, N, M, Q, S, T, V and Y.

In other preferred embodiments, X2 means an amino acid residue selected in the group consisting of N, A, E, F and I.

In further preferred embodiments, X2 means the amino acid residue N or A.

Similarly, the identity of the two neutral amino acids X5 and X6 located at the C-terminal end of a V2R antagonist peptide disclosed herein shall not substantially affect the binding ability of the said peptide to V2R.

In most preferred embodiments, the present disclosure concerns peptides having 80% amino acid identity or more with the peptide of SEQ ID NO. 1 and comprising no deletion and no addition of an amino acid residue as compared with the peptide of SEQ ID NO. 1. Thus, most preferably, a V2R antagonist peptide according to the present disclosure has 57 amino acids in length, the amino acid sequence thereof comprising no amino acid deletion and no amino acid addition as compared with SEQ ID NO. 1

Peptides having an amino acid sequence which has 80% amino acid identity with SEQ ID NO. 1 most preferably consist of peptides exclusively differing from the peptide of SEQ ID NO. 1 by the presence of one or more substitutions of an amino acid residue as compared with SEQ ID NO. 1, thus peptides having 57 amino acid residues in length and comprising one or more amino acid substitutions as compared with SEQ ID NO. 1.

A peptide whose sequence has 80% amino acid identity with SEQ ID NO. 1 may comprise up to 11 amino acid substitutions as compared with SEQ ID NO. 1. The present disclosure encompasses peptides having 1, 2, 3, 4, 5, 6, 7, 8, 9, 10 or 11 substitutions of one amino acid residue as compared with SEQ ID NO. 1.

The disclosure thus encompasses V2R antagonist peptides comprising an amino acid sequence having 80% or more amino acid identity with SEQ ID NO. 1 and comprising one or more modification into one or more amino acid residues, peptide bonds, N- and/or C-terminal ends of the protein, as long as the V2R antagonist activity is maintained. These modifications which are introduced into the peptide by the conventional methods known to those skilled in the art, include, in a non-limiting manner the substitution of a natural amino acid with a non-proteinogenic amino acid (D amino acid or amino acid analog); the modification of the peptide bond, in particular with a bond of the retro or retro-inverso type or a bond different from the peptide bond; the cyclization, and the addition of a chemical group to the side chain or the end(s) of the protein, in particular for coupling an agent of interest to a V2R peptide antagonist described herein. These modifications may be used to label the V2R antagonist peptide, or alternatively to further increase its affinity for V2R, its bioavailability and/or its stability.

In some embodiments, in a V2R antagonist peptide as disclosed herein; one or more amino acid residues targeted by endoproteases are replaced by their corresponding non-natural D-form. For example, one or more arginine and/or lysine residues which are targets for trypsin can be replaced by their corresponding non-natural form.

In some embodiments, in a V2R antagonist peptide as disclosed herein, one or more disulfide bridges are replaced by non-natural links. Preferably, said non-natural link is resistant to reduction, such as, for example, a thiazolidine linker. These linkers increase the resistance of the protein of the invention to reducing agents present in biologic fluids.

Most preferably, a V2R antagonist peptide according to the present disclosure, which encompasses peptides comprising one or more amino acid substitutions as compared with SEQ ID NO. 1, comprises cysteine residues located at the amino acid positions corresponding to positions 5 and 55 of SEQ ID NO. 1.

Most preferably, a V2R antagonist peptide according to the present disclosure, which encompasses peptides comprising one or more amino acid substitutions as compared with SEQ ID NO. 1, comprises cysteine residues located at the amino acid positions corresponding to positions 14 and 38 of SEQ ID NO. 1.

Most preferably, a V2R antagonist peptide according to the present disclosure, which encompasses peptides comprising one or more amino acid substitutions as compared with SEQ ID NO. 1, comprises cysteine residues located at the amino acid positions corresponding to positions 30 and 51 of SEQ ID NO. 1.

In some embodiments of a peptide as disclosed herein, X1 means the amino acid residue G (Glycine).

In some embodiments of a peptide as disclosed herein, X2 means the amino acid residue A (Alanine).

In some embodiments of a peptide as disclosed herein, X3 means the amino acid D (Aspartic acid).

In some embodiments of a peptide as disclosed herein, X4 means the amino acid residue E (Glutamic acid) or L (Leucine).

The present disclosure also relates to a peptide comprising the amino acid sequence of SEQ ID NO. 1, wherein each of X1 to X6, one independently from the others, have the meanings described for SEQ ID NO. 1. It also pertains to a peptide consisting of the amino acid sequence of SEQ ID NO. 1, wherein each of X1 to X6, one independently from the others, have the meanings described for SEQ ID NO. 1.

The present disclosure also concerns a peptide having 80% or more amino acid identity with the amino acid sequence of SEQ ID NO. 1, wherein X1 means F, X2 means N, X3 means T, X4 means I, and X5 and X6 have the same meaning as for SEQ ID NO.1. Most preferably, X5 means V and X6 means G. The present disclosure further concerns a peptide having 80% amino acid identity with the peptide of SEQ ID NO. 2, which encompasses a peptide consisting of SEQ ID NO. 2.

The present disclosure also relates to a peptide having 80% or more amino acid identity with the amino acid sequence of SEQ ID NO. 1 wherein X1 means F, X2 means N, X3 means T, X4 means L, and X5 and X6 have the same meaning as for SEQ ID NO.1. Most preferably, X5 means V and X6 means G. The present disclosure further relates to a peptide having 80% or more amino acid identity with the peptide of SEQ ID NO. 3. It also pertains to a peptide consisting of the amino acid sequence of SEQ ID NO. 3.

The present disclosure also relates to a peptide having 80% or more amino acid identity with the amino acid sequence of SEQ ID NO. 1 wherein X1 means F, X2 means A, X3 means T, X4 means L, and X5 and X6 have the same meaning as for SEQ ID NO.1. Most preferably, X5 means V and X6 means G. The present disclosure further relates to a peptide having 80% or more amino acid identity with the peptide of SEQ ID NO. 4. It also pertains to a peptide consisting of the amino acid sequence of SEQ ID NO. 4.

The present disclosure also relates to a peptide having 80% or more amino acid identity with the amino acid sequence of SEQ ID NO. 1 wherein X1 means G, X2 means N, X3 means D and X4 means I, and X5 and X6 have the same meaning as for SEQ ID NO.1. Most preferably, X5 means V and X6 means G. The present disclosure further relates to a peptide having 80% or more amino acid identity with the peptide of SEQ ID NO. 5. It also pertains to a peptide consisting of the amino acid sequence of SEQ ID NO. 5.

The present disclosure also relates to a peptide having 80% or more amino acid identity with the amino acid sequence of SEQ ID NO. 1 wherein X1 means G, X2 means N, X3 means D, X4 means E, and X5 and X6 have the same meaning as for SEQ ID NO.1. Most preferably, X5 means V and X6 means G. The present disclosure further relates to a peptide having 80% or more amino acid identity with the peptide of SEQ ID NO. 6. It also pertains to a peptide consisting of the amino acid sequence of SEQ ID NO. 6.

The present disclosure also relates to a compound of the following formula (I):

$$[Nt\text{-}EXT]n\text{-}L1x\text{-}[V2R\text{-}AP]\text{-}L2y\text{-}[Ct\text{-}EXT]m \qquad (I),$$

wherein:

[Nt-EXT] means a chemical moiety which is covalently linked to the N-terminal end of a V2R antagonist peptide as disclosed herein,

[V2R-AP] means a V2R antagonist peptide according to the present disclosure,

[Ct-EXT] means a chemical moiety which is covalently linked to the C-terminal end of a V2R antagonist peptide as disclosed herein, and each of n and m, independently mean an integer equal to 0 or 1, Each of L1 and L2 is a linker moiety which, when present, may avoid inhibiting interactions (i) between [Nt-EXT] and [V2R-AP] and (ii) between [Ct-EXT] and [V2R-AP], respectively, and. Further importantly, each of L1 and L2, when present, is useful for preventing any of [Nt-EXT] and [Ct-EXT] affecting the binding of the V2R antagonist peptide [V2R-AP] to the V2R.

each of x and y, independently mean an integer equal to 0 or 1.

In some preferred embodiments [Nt-EXT] and/or [Ct-EXT], when present, independently mean a non-protein chemical moiety, such as a non-protein detectable molecule which is used for labeling a V2R antagonist peptide, like a radioactive chemical moiety or a fluorophore-containing chemical moiety, or a stabilization moiety such as ZZ, DsBa and DsBb. In some of these embodiments, [Nt-EXT] and/or [Ct-EXT] is an agent which increases the bioavailability of a V2R antagonist peptide as described herein, and in particular which reduces its urinary elimination, such as, for example, a polyethylene glycol molecule. In some preferred embodiments, [Nt-EXT] and/or [Ct-EXT], when present, may independently mean a polyalkylene glycol, and especially a polyethylene glycol. These preferred embodiments encompass a polyethylene glycol of formula H—(O—CH$_2$—CH$_2$)n-O— wherein n is an integer ranging from 5 to 20, advantageously from 10 to 15, such as n consisting of an integer meaning 12.

In some other preferred embodiments, [Nt-EXT] and/or [Ct-EXT], when present, independently mean a protein moiety, which encompasses protein/peptide moieties including those which allow the purification, detection, immobilization, and/or cellular targeting of the protein of the invention, and/or which increase the affinity for V2R, the bioavailability, the production in expression systems and/or stability of the V2R antagonist peptide. These protein moieties may be selected from: (i) a labeling moiety such as a fluorescent protein (GFP and its derivatives, BFP and YFP), (ii) a reporter moiety such as an enzyme tag (luciferase, alkaline phosphatase, glutathione-transferase (GST), β-galactosidase), (ii) a binding moiety such as an epitope tag (polyHis6, FLAG, HA, myc), a DNA-binding domain, a hormone-binding domain, a poly-lysine tag for immobilization onto a support, and (iii) a targeting moiety for addressing the compound of formula (I) to a specific cell type or cell compartment. In addition, the compound of formula (I) advantageously comprise a linker (L1, L2) which links each of [Nt-EXT] and/or [Ct-EXT] to [V2R-AP] which linker is long enough to avoid inhibiting interactions between sequence [V2R-AP] and each of [Nt-EXT] and/or [Ct-EXT], when present. The linker L1 and/or L2 may also comprise a recognition site for a protease, for example, for removing affinity tags and stabilization moieties from the purified chimeric protein according to the present invention.

In some embodiments, a linker moiety L1 and/or L2 may comprise a recognition site for a protease, for example, for removing affinity tags and stabilization moieties from a compound of formula (I) according to the present disclosure.

In addition, a V2R antagonist peptide as described herein, or some embodiments of a compound of formula (I), may advantageously be modified by means well-known to those skilled in the art, in order to change its physiological properties, and in particular in order to improve its half-life time in the organism (glycosylation: HAUBNE R. et al, J. Nucl. Med., 2001, 42, 326-36; conjugation with PEG: KIM TH. et al, Biomaterials, 2002, 23, 2311-7), its solubility (hybridization with albumin: KOEHLER MF. et al, Bioorg. Med. Chem. Lett., 2002, 12, 2883-6), its resistance to proteases (unnatural amino acids (D conformation, for example)), and/or its intestinal absorption (Lien et al, TIB, 2003, 21, 556-).

Synthesis of a V2R Antagonist Peptide

A V2R antagonist peptide as described herein can be produced by a known cloning technology or by chemical synthesis.

For example, DNA encoding a V2R antagonist peptide is prepared by use of a cloning technology and inserted into an autonomously replicable vector to prepare a recombinant DNA. The recombinant DNA is introduced into an appropriate host, such as *Escherichia coli, Bacillus subtilis, Actinomyces*, yeast, filamentous fungus, a plant cell, an insect cell and an animal cell, to obtain a transformant. From the cultured product of the transformant, a V2R antagonist peptide as disclosed herein can be obtained. Alternatively, DNA encoding a V2R antagonist peptide is prepared and subjected to an acellular protein-synthesis system using wheat germ and a cell extract from *Escherichia coli*, to synthesize the peptide according to the disclosure.

The disclosure encompasses the use of a nucleic acid encoding a V2R antagonist peptide as described herein in expressible form or a recombinant vector comprising the said nucleic acid. The nucleic acid encoding a V2R antagonist peptide in expressible form refers to a nucleic acid molecule which, upon expression in a cell or a cell-free system results in a functional peptide.

Indeed, in the embodiments wherein a compound of formula (I) consists of a protein, the said compound of formula (I) may also be produced as a recombinant protein, according to the same methods as above.

Moreover, using a customary chemical synthesis method for a V2R antagonist peptide as disclosed herein, such as a "solid phase method" or "a liquid phase method", amino acids are successively connected and extended by dehydration/condensation. A method of synthesis of V2R antagonist peptides by chemical synthesis is described in the examples herein.

Pharmaceutical Compositions

The present disclosure further relates to the use of a V2R antagonist peptide described herein, or in some embodiments a compound of formula (I) including the said V2R antagonist peptide, for medical purposes, and especially for treating pathologic conditions involving the V2R pathway.

The disclosure also encompasses the use of a nucleic acid encoding a V2R antagonist peptide as described herein, or alternatively some protein embodiments of a compound of formula (I), in expressible form, or a recombinant vector comprising the said nucleic acid. The nucleic acid encoding such a protein in expressible form refers to a nucleic acid molecule which, upon expression in a cell or a cell-free system results in a functional protein, i.e. a protein consisting of a V2R antagonist.

Thus, according to the present disclosure, the said protein, the said nucleic acid and/or the said recombinant vector may be included in a pharmaceutical composition, further comprising a pharmaceutically acceptable carrier.

A pharmaceutical composition according to the present disclosure may be formulated for administration by a number of routes, including, but not limited to, enteral (e.g., oral), parenteral, intravenous, intramuscular, intra-arterial, subcutaneous, transdermal, intradermal, rectal, intravaginal, intraperitoneal, topical, mucosal, nasal, buccal, sublingual; and/or inhalation; and/or as an oral spray, nasal spray, and/or aerosol.

In some embodiments, a pharmaceutical composition according to the disclosure may be in any suitable form encompassed by the state in the art, e.g. in the form of an injectable solution or suspension, a tablet, a coated tablet, a capsule, a syrup, a suppository, a cream, an ointment, a lotion, and the like.

Pharmaceutical compositions comprising a V2R antagonist peptide or a selected compound of formula (I) may be presented in a powder form of a lyophilizate wherein the active ingredient is combined with a sugar such as mannitol. For its use, such a pharmaceutical composition shall be generally reconstituted with an appropriate volume of water or of chloride sodium solution. Then, the resulting liquid pharmaceutical composition may be administered by the appropriate administration route.

In a pharmaceutical composition, a V2R antagonist peptide or a selected compound of formula (I) is combined with one or more pharmaceutically acceptable carriers, and optionally sustained-release matrices, such as biodegradable polymers, to form therapeutic compositions.

In certain embodiments, the pharmaceutical composition may further comprise one or more salts, one or more buffering agents, and/or one or more preservatives.

The pharmaceutically acceptable carriers are those known from the skilled person and which are conventionally used.

Within the scope of the instant disclosure, a "pharmaceutically acceptable carrier" refers to a pharmaceutically acceptable material, composition or vehicle, such as a liquid or solid filler, diluent, excipient, solvent or encapsulating material, involved in carrying or transporting a prophylactically or therapeutically active agent.

In certain embodiments, a suitable pharmaceutically acceptable carrier may be selected in a group including sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide and aluminum hydroxide; pyrogen-free water; isotonic saline; Ringer's solution; ethyl alcohol; phosphate buffer solutions; and the like.

A pharmaceutical composition according to the present disclosure comprises a therapeutically effective amount of a V2R antagonist peptide described herein, or of a selected embodiment of a compound of formula (I), or of a nucleic acid or a recombinant vector encoding the same, e.g., an amount sufficient to exert a medical benefit to the individual to whom it is administered. The pharmaceutically effective dose depends upon the kind of composition used, the route of administration, whether the administration is in single or multiple doses, the type of mammal (human or non-human mammal) being treated, the physical characteristics of the individual's parameters including age, physical condition, size, weight, concurrent medication, and other factors, that those skilled in the medical arts will recognize. Thus, within the scope of the instant disclosure, the effective amount of the active ingredient to be administered, especially the amount of an V2R antagonist peptide or of the selected compound of formula (I), may be determined by a physician or an authorized person skilled in the art and can be suitably adapted within the time course of the treatment.

A V2R antagonist peptide, or a selected compound of formula (I), may be administered at an amount per administration step ranging from 0.1 to 300 nanomoles of the selected V2R antagonist peptides per kg of body weight, depending of the above-described individual parameters. The inventors believe that administering a V2R antagonist peptide as disclosed herein at an amount lower than 0.1 nanomole per kg of body weight will not be therapeutically effective. The inventors also believe that administering a V2R antagonist peptide as disclosed herein at an amount higher than 300 nanomoles per kg of body weight may cause undesirable effects, and possibly some toxic effects, to occur in the subject.

Indeed, the exact molecular weight (Mw) of each of the V2R antagonist peptide as disclosed is always determinable.

Assuming a V2R antagonist peptide according to the present disclosure having a Mw of 6500, administering 0.1 nanomole/kg thereof to a subject weighing 80 kg consists of administering 52 ng of the said peptide to the said subject. Still assuming a V2R antagonist peptide according to the present disclosure having a Mw of 6500, administering 300 nanomole/kg thereof to a subject weighing 80 kg consists of administering 0.156 mg of the said peptide to the said subject.

For the sake of clarity, in some embodiments wherein a selected active ingredient comprises a V2R antagonist peptide according to the present disclosure, the amount of active ingredient to administer to a subject in need thereof is calculated on the basis of the Mw value of the V2R antagonist peptide comprised therein, and not on the basis of the Mw value of the active ingredient per se. Illustratively, in some embodiments wherein a selected active ingredient is a compound of formula (I) as disclosed herein, the amount of active ingredient to administer to a subject in need thereof is calculated on the basis of the Mw value of the [V2R-AP] moiety comprised therein, and not on the basis of the Mw value of the active ingredient per se.

As used herein, an amount of a selected V2R antagonist peptide of 0.1 nmole/kg or more encompasses amounts of 0.5, 1, 2, 3, 4, 5, 6, 7, 8, 9, 10, 15 or 20 nmoles/kg or more of the said selected V2R antagonist peptides.

As used herein, an amount of a selected V2R antagonist peptide of 300 nmoles/kg or less encompasses amounts of 290, 280, 270, 260, 250, 240, 230, 220, 210, 200, 150 nmoles/kg or less of the said selected V2R antagonist peptides.

Medical Uses

The present disclosure pertains to the use of a V2R antagonist peptide described herein, or a selected compound of formula (I) described herein, for preparing a medicament. It also concerns a V2R antagonist peptide described herein, or a selected compound of formula (I) described herein, for use as a medicament.

The present disclosure also relates to a method for treating a subject affected with a pathological condition involving the V2R pathway comprising a step of administering a V2R antagonist peptide described herein, or a selected compound of formula (I) described herein, or a nucleic acid or a recombinant vector encoding the same, to the said subject.

This disclosure also pertains to the use of a V2R antagonist peptide described herein, or a selected compound of formula (I) described herein, or a nucleic acid or a recombinant vector encoding the same, for preparing a medicament for treating a subject affected with a pathological condition involving the V2R pathway.

This disclosure further concerns a V2R antagonist peptide described herein, or a selected compound of formula (I) described herein, or a nucleic acid or a recombinant vector encoding the same, for its use for treating a subject affected with a pathological condition involving the V2R pathway.

In some embodiments, the active ingredient, i.e. a V2R antagonist peptide as described herein or a selected compound of formula (I), may be administered as a single bolus, as several divided doses administered over time, or the dose may be proportionally reduced or increased as indicated by the exigencies of the therapeutic situation. It may be particularly advantageous to formulate a therapeutic agent in a dosage unit form for ease of administration and uniformity of dosage. Dosage unit form, as used herein, refers to physically discrete units suited as unitary dosages for the mammalian subjects to be treated, each unit containing a predetermined quantity of active compound calculated to produce the desired therapeutic effect in association with the required pharmaceutical carrier. The specification for the dosage unit forms of the present disclosure may be dictated by and directly dependent on (a) the unique characteristics of the active ingredient and the particular therapeutic effect to be achieved, and (b) the limitations inherent in the art of compounding such an active ingredient for the treatment of sensitivity in individuals.

Thus, the skilled artisan would appreciate, based upon the disclosure provided herein, that the dose and dosing regimen is adjusted in accordance with methods well known in the therapeutic arts. That is, the maximum tolerable dose may be readily established, and the effective amount providing a detectable therapeutic benefit to a subject may also be determined, as can the temporal requirements for administering each agent to provide a detectable therapeutic benefit to the subject.

Determining appropriate dosages and regimens for administration of the chemotherapeutic agent are well-known in the relevant art and would be understood to be encompassed by the skilled artisan once provided the teachings disclosed herein.

Pathologies involving the V2R pathway include, with no limitations: (i) pathological conditions characterized by euvolemic or hypovolemic hyponatremia, such as congestive heart failure (CHF), cirrhosis, Syndrome of Inappropriate Antidiuretic Hormone secretion (SIADH) and cerebral oedema, (ii) Nephrogenic Syndrome of Inappropriate Antidiuresis (NSIAD), (iii) Congenital Nephrogenic Diabetes Insipidus (cNDI), (iv) Polycystic kidney disease, (v) cancers, including renal and lung cancers, (vi) thrombosis, (vii) Meniere disease, (viii) refractory liver disease and (ix) heart failure.

Diagnostic

According to further aspects, this disclosure relates to the use of a V2R antagonist peptide, or alternatively of a selected compound of formula (I), as a diagnostic or imaging reagent that can be applied in optical imaging, magnetic resonance imaging (MRI) and positron emission tomography (PET) for detecting V2R cell expression under physiological or pathological conditions or in response to an endogenous or exogenous stimulus, for diagnostic or research purposes. It may also be used as a drug screening tool, for screening V2R ligands, including V2R agonists and antagonists.

In a preferred embodiment, the V2R antagonist peptide is labeled by coupling to a detectable molecule.

Then, the present disclosure further relates to a labeled V2R antagonist peptide as described herein.

Conventional detectable molecules (labels) may be used which are capable, alone or in concert with other compositions or compounds, of providing a detectable signal. Suitable detection methods include, e.g., detection of an agent which is tagged, directly or indirectly, with a fluorescent label by immunofluorescence microscopy, including confocal microscopy, or by flow cytometry (FACscan); detection of a radioactively labeled agent by autoradiography; electron microscopy; immunostaining; subcellular fractionation, or the like. In some embodiments, a radioactive element (e.g. a radioactive amino acid) is incorporated directly into a peptide chain; in other embodiments, a fluorescent label may be associated with a peptide via biotin/avidin interaction, association with a fluorescein conjugated peptide, or the like.

In embodiments of the disclosure, the detection procedure comprises visibly inspecting the labelled agent for a colour change, or inspecting the labelled V2R peptide antagonist for a physical-chemical change. Physical-chemical changes may occur with oxidation reactions or other chemical reactions. They may be detected by eye, using a spectrophotometer, or the like.

Thus, a useful detectable molecule for labeling a V2R antagonist peptide described herein is preferably a labeling agent which produces a detectable and/or quantifiable signal, in particular a radioactive, magnetic or luminescent (radioluminescent, chemiluminescent, bioluminescent, fluorescent or phosphorescent) agent. The labeled protein may be labeled directly or indirectly, via covalent or non-covalent bonds, using standard conjugation techniques that are well-known to those skilled in the art. Examples of labeling agents include radioactive isotopes such as Technetium-99 ($^{99}$Tc), Fluorine-18 ($^{18}$F), Tritium ($^3$H) and Iodine-125 ($^{125}$I); luminescent agents such as AlexaFluor, FITC and cyanine 3; paramagnetic contrast agents such as gadolinium compounds, and superparamagnetic contrast agents such as iron oxide nanoparticles.

For the sake of clarity, a V2R antagonist peptide as disclosed herein that is coupled to a detectable molecule may consist of an embodiment of a compound of formula (I) wherein at least one of [Nt-EXT] or [Ct-EXT] is present (i.e. with at least one of integers m or n which means 1) and comprises, or consists of, the said detectable molecule.

In some preferred embodiments, in the labeled agent, the V2R antagonist peptide is linked covalently to a radioactive or a fluorescent agent.

Covalent coupling of the labeling agent, for example a fluorescent or radioactive agent, to the V2R antagonist peptide may be achieved by: (i) incorporating the labeling agent at the N- or C-terminal end of the protein during chemical synthesis of the protein, or (ii) incorporating a reactive group (free cysteine.biotinyl, azido moiety) in a recombinant or synthetic protein, and then using the group to link the labeling agent covalently.

Preferably, the labeling agent is linked covalently to the N- or C-terminus of the protein as none the N-terminal end nor the C-terminal end of the V2R antagonist peptide is involved in its binding to V2R.

This disclosure relates to the use of a labeled V2R antagonist peptide described herein for detecting cells expressing V2R, in vitro or in vivo. It also pertains to the use of a labeled V2R antagonist peptide described herein, in vitro or in vivo, for measuring the V2R expression level by cells expressing V2R.

This disclosure also concerns an in vitro method for detecting a dysregulation of vasopressin-2 receptor cell expression comprising the steps of:

a) providing cells to be tested, b) bringing the cells provided at step a) with a labeled V2R antagonist peptide according to the present disclosure, c) measuring the expression level value of vasopressin-2 receptor by the cells provided at the end of step b), d) comparing the expression level value obtained at step c) with a reference expression level value, e) determining the occurrence of a dysregulation of vasopressing-2 receptor cell expression.

In some embodiments, the reference expression level value which is used at step d) consists of the mean V2R expression level value which is expected in cells of a subject which is not affected with a dysregulation of V2R cell expression, i.e. of a subject which is not affected with a disorder or a disease involving the V2R pathway.

In some other embodiments, the reference expression level value which is used at step d) consists of a V2R expression value which is known, or otherwise determined or determinable, in cells of a subject which is affected with a dysregulation of V2R cell expression, i.e. of a subject which is affected with a disorder or a disease involving the V2R pathway.

As it is well known in the art, ectopic expression of AVP and its receptors has been reported in numerous cancers (North et al., 1999, Peptides, Vol. 20: 837-842; Sinha et al., 2019, Oncogene, Vol. 30(6): 1231-1245) with a potential anti-proliferative effect for V2R agonists in breast, pancreatic, colorectal and lung cancers (Garona et al., 2015, Int J Oncol, Vol. 46: 2335-2345; Ripoll et al., 2013, Breast Cancer Res Treat, Vol. 142: 9-18; Iannucci et al., 2011, Future Med Chem, Vol. 3: 1987-1993; Garona et al., 2018, Cancer Res Treat, Vol. 51(2): 438-450; Pifano et al., 2017, Front Oncol, 7: 11; Garona et al., 2020, in Vitamins and Hormones, Vol. 113: 259-289) and an anti-proliferative effect for V2R antagonists in human renal carcinomas (Sinha et al., 2019, Oncogene, Vol. 30(6): 1231-1245). In this context, a V2R antagonist peptide according to the present disclosure readily constitutes an interesting probe for imaging cancer cells overexpressing V2R.

Another subject of the present disclosure relates to the use of a V2R antagonist peptide as described herein in an in vitro diagnosis method.

Another subject of the present disclosure is also the in vitro or in vivo use of a V2R antagonist peptide described herein, or of a selected compound of formula (I) described herein, for diagnosing a pathology involving an increase or a decrease in V2R expression level.

A further subject of the present disclosure is the V2R antagonist peptide, or a selected compound of formula (I) described herein for use, in vitro or in vivo, for diagnosing a pathology involving an increase or decrease in V2R expression level For some diagnostic applications, the labeled V2R antagonist peptide is used to visualize V2R expression, in vitro or in vivo, in a tissue from a patient, and evaluate its expression level in comparison to the same type of tissue from an healthy individual. V2R overexpression is indicative of a pathological condition such as cancer, whereas V2R underexpression is indicative of a pathological condition such as Congenital Nephrogenic Diabetes Insipidus (cNDI). Once, the diagnostic has been established, it is possible to decide on an effective treatment for the diagnosed patient, including the use of V2R antagonists, for example for treating cancer or cNDI.

A subject of the present invention is also the use of the V2R antagonist peptide, as a research tool for studying V2R.

Another subject of the present disclosure is a method for detecting V2R, in vitro or in vivo, comprising the steps of:

a) bringing cells to be analyzed into contact with the labeled V2R antagonist peptide, and b) detecting the labeled cells.

The labeling of the cells is in particular fluorescent labeling or magnetic labeling, detectable by any technique known to those skilled in the art (fluorescence microscopy, flow cytometry, magnetic resonance imaging).

The detection of the V2R receptors, in vivo, in the body of a mammal (cell imaging), in particular in real time, comprises a prior step of administering said labeled V2R antagonist peptide to said mammal (parenteral injection, oral administration).

Another subject of the present disclosure is the use of a V2R antagonist peptide as disclosed herein for screening V2R ligands.

A subject of the present disclosure is also a method for screening V2R ligands, comprising:

a) incubating V2R with a test molecule and a labeled V2R antagonist peptide of the present disclosure, and b) measuring the signal obtained respectively in the presence and in the absence of the test molecule, wherein a lower signal in the presence of the molecule compared to the control without the test molecule indicates that the test molecule is a V2R ligand.

The agonist, antagonist effect of the identified ligands on V2R are then tested in cells expressing V2R using pharmacological assays which are well-known in the art such as those disclosed in the examples of the present application.

The present disclosure provides also a kit comprising: (a) a first container that contains one or more of: a V2R antagonist peptide, a nucleic acid or a recombinant vector encoding the same, a modified host cell, pharmaceutical composition, diagnostic or imaging reagent as described herein, in solution or in lyophilized form; (b) optionally, a second container containing a diluent or reconstituting solution for the lyophilized formulation; (c) optionally a third container containing an isolated V2R receptor or host cell capable of expressing V2R in solution or in lyophilized form, and optionally instructions for the use of the solution(s) and/or the reconstitution and/or use of the lyophilized formulation(s).

The present disclosure is further illustrated by, without in any way being limited to, the examples herein.

EXAMPLES

Example 1: Activity of V2R Antagonist Peptides

A. Materials and Methods

Chemical Synthesis of Peptides.

Peptide synthesis was performed on a Gyros Protein Technologies, Inc Prelude synthesizer at a 12.5 μmole scale, deprotected, purified and folded as described (Ciolek et al., 2017, Proc Natl Acad Sci USA, Vol. 114: 7154-7159).

Peptide batches with purities higher than 95% were used all along the experiments. The 6-azidohexanoic was coupled on the resin after the automatic synthesis of the MQ1 and the deprotection of the N-terminal amine function. 2 eq of 6-azidohexanoic was coupled twice for 60 minutes with the coupling agent HCTU (1.9 eq) in the presence of 2 eq of diisopropylethylamine. The 6-Azidohexanoic-MQ1 was cleaved from the resin, purified and oxidized as for the MQ1 V2R peptide antagonist. 10 eq of DFO-DBCO (p-isothiocyanatobenzyldesferrioxamine-diarylbicyclooctyne, dissolved in 200 μl DMF), or of Cy5.5-DBCO (dissolved in 200 μl HEPES buffer) or of AFDye-488-DBCO (dissolved in 200 μl HEPES buffer) were mixed with 0.3 μmol of 6-azidohexanoic-MQ1 dissolved in HEPES buffer (200 μl, pH 7.4) and leaved overnight at room temperature and purified by HPLC.

B. Results

A variety of MQ1-derived peptides have been tested for their binding affinity to the human vasopressin-2 receptor (V2R).

The results are summarized in Table 1 hereunder.

| peptides | Ki, nM | ratio | sequence | SEQ ID NO. |
|---|---|---|---|---|
| WT MQ1 peptide (prior art) V2R antagonist peptides of this disclosure | 5.02 | 1.00 | RPSFCNLPVKPGPCNGFFSAFYYSQKTNKCHSFTYGGCKGNANRFSTIEKCRRTCVG | 7 |
| K39A | 0.57 | 0.115 | RPSFCNLPVKPGPCNGFFSAFYYSQKTNKCHSFTYGGCAGNANRFSTIEKCRRTCVG | 2 |
| K39A + I48L | 0.93 | 0.19 | RPSFCNLPVKPGPCNGFFSAFYYSQKTNKCHSFTYGGCAGNANRFSTLEKCRRTCVG | 3 |

-continued

| peptides | Ki, nM | ratio | sequence | SEQ ID NO. |
|---|---|---|---|---|
| N15A + K39A + I48L | 2.05 | 0.41 | RPSFCNLPVKPGPCAGFFSAFYYSQKTNKCHSFTYGGCAGNANRFSTLEKCRRTCVG | 4 |
| F4G K39A T27D | 0.74 | 0.15 | RPSGCNLPVKPGPCNGFFSAFYYSQKDNKCHSFTYGGCAGNANRFSTIEKCRRTCVG | 5 |
| MQ-LEAD F4G + K39A + T27D + I48E Comparative peptides | 0.66 | 0.13 | RPSGCNLPVKPGPCNGFFSAFYYSQKDNKCHSFTYGGCAGNANRFSTEEKCRRTCVG | 6 |
| K10A | 9.38 | 1.87 | RPSFCNLPVAPGPCNGFFSAFYYSQKTNKCHSFTYGGCKGNANRFSTLEKCRRTCVG | 8 |
| K10E | 337 | 67 | RPSFCNLPVEPGPCNGFFSAFYYSQKTNKCHSFTYGGCKGNANRFSTLEKCRRTCVG | 9 |
| F17A | 6684 | 1331 | RPSFCNLPVKPGPCNGAFSAFYYSQKTNKCHSFTYGGCKGNANRFSTLEKCRRTCVG | 10 |
| F18A | 152 | 30 | RPSFCNLPVKPGPCNGFASAFYYSQKTNKCHSFTYGGCKGNANRFSTLEKCRRTCVG | 11 |
| N41A | 8.49 | 1.69 | RPSFCNLPVKPGPCNGFFSAFYYSQKTNKCHSFTYGGCKGAANRFSTIEKCRRTCVG | 12 |
| R44A | 13.3 | 2.6 | RPSFCNLPVKPGPCNGFFSAFYYSQKTNKCHSFTYGGCKGNANAFSTLEKCRRTCVG | 13 |
| R44E | 99.3 | 19.8 | RPSFCNLPVKPGPCNGFFSAFYYSQKTNKCHSFTYGGCKGNANEFSTLEKCRRTCVG | 14 |

In case of a discrepancy between the sequences disclosed in Table 1 and those described in a sequence listing, the correct sequences are those listed in Table 1.

The results depicted in Table 1 show that the most efficient peptides tested, which present a $IC_{50}$ ratio value of 0.5 or less, as compared to the known MQ1 V2R antagonist peptide, are all peptides wherein the lysine residue located at the amino acid position 39 in the known MQ 1 V2R antagonist peptide is replaced by an alanine residue (amino acid change conventionally denoted "K39A"). The most effective V2R antagonist peptides are the following:

"K39A" peptide of the amino acid sequence of SEQ ID NO. 2,

"K39A+I48L" peptide of the amino acid sequence of SEQ ID NO. 3,

"N15A+K39A+I48L" peptide of the amino acid sequence of SEQ ID NO. 4,

"F4G+K39A+T27D" peptide of the amino acid sequence of SEQ ID NO. 5.

"F4G+K39A+T27D I48E" peptide, also termed "MQ-LEAD" herein, of the amino acid sequence of SEQ ID NO. 6, and

Example 2: Immunogenicity and Selectivity of V2R Antagonist Peptides

A. Materials and Methods
A.1. Immunogenicity

The immunogenicity of therapeutic proteins remains a major risk of failure for their development and is therefore a very important concern for the pharmaceutical industry. Immunogenicity is the ability of molecules to induce an immune response. The antibodies (Anti Drug Antibody or ADA) resulting from this response can inhibit the therapeutic activity of the proteins or even induce allergic symptoms. As immune responses are species-dependent, animals such as mice and rats are very poor predictive models of immunogenicity and do not allow the immunogenicity of molecules to be evaluated when injected into humans. The pre-clinical evaluation of immunogenicity is based on the mechanisms regulating the immune response in humans.

ADA responses against therapeutic proteins primarily involve three different cell types i) B cells that produce antibodies, ii) CD4 T cells that provide the necessary assistance to B cells to secrete the antibodies, and iii) dendritic cells that, by presenting the proteins as peptides to the T cells, cause their activation. When a protein is injected into the body, the protein is taken up by the dendritic cells and is broken down into peptides. Some of the peptides generated have appropriate anchor residues to bind to HLA class II molecules and are presented to T cells.

Peptides recognized by T cells are called T epitopes. Because HLA class II molecules are polymorphic, T epitopes vary from molecule to molecule and therefore vary between individuals based on their HLA class II molecules.

Given the role of T lymphocytes in the ADA response, the immunogenicity of therapeutic proteins is highly dependent on their ability to activate T lymphocytes and thus to contain T epitopes in their sequence. An evaluation of the T epitope content can be done using predictive software, the most efficient of which is NETMHC. The presence of potential T epitopes in U-Da2a and MQ-LEAD were tested by NETMHC software.

A.2. Selectivity

The protease assay general protocol is the following:

1 Deliver 2× Enzyme

2 Deliver buffer into No Enzyme wells

3 Deliver MQ-WT (U-Da2a) in water by using Acoustic technology (Echo550; nanoliter range)

4 Incubate for 5-15 min

5 Deliver 2× Substrate to initiate the reaction

6 Spin & shake, start measuring in EnVision at room temp; 5 min interval for 25 (2 hours)

7 Analyze data by taking slope*(signal/time) of linear portion of measurement

8 Slope is calculated by using Excel, and curve fits are performed using Prism software The specific specifications are disclosed in Table 2, at the end of the present disclosure Buffer:

A 25 mM Tris pH 8.0, 100 mM NaCl, 0.01% Brij35,

B' 25 mM MES pH 6, 50 mM NaCl, 0.005% Brij35, 5 mM DTT

B 75 mM Tris pH 7.0, 0.005% Brij35, 3 mM DTT

B+EDTA 75 mM Tris pH 7.0, 1 mM EDTA, 0.005% Brij35, 3 mM DTT

C 100 mM Tris-HCl, pH 8.0, 50 mM NaCl, 10 mM CaCl2, 0.025% CHAPS, 1.5 mM DTT

D 25 mM Sodium Acetate pH 5.5, 0.1 M NaCl, 5 mM DTT

E 25 mM Sodium Acetate pH 3.5, 5 mM DTT

F 25 mM Tris pH 9,150 mM NaCl

L 400 mM NaAcetate pH 5.5, 4 mM EDTA, 8 mM DTT

X (Furin) 100 mM Tris-HCl, pH 7.5, 1 mM CaCl2, 0.5% TX-100, 1 mM DTT

S 0.1 M Sodium Acetate pH 3.5, 0.1 M NaCl

TCN 25 mM Tris pH 7.5, 10 mM CaCl2, 150 mM NaCl

TCNB 25 mM Tris pH 7.5, 10 mM CaCl2, 150 mM NaCl, 0.05% Brij35

Z 25 mM Tris pH 9, 2.5 uM ZnCl2, 0.005% Brij

KLK 7 buffer 50 mM Tris, 150 mM NaCl, pH 8.5

ACE2 Buffer 75 mM Tris, pH 8.5, 1 M NaCl

Neprilysin Buffer 50 mM Tris, pH 9.0

CTSD buffer 100 mM Sodium Acetate pH 3.5, 200 mM NaCl, 0.02% Brij35

CTSE buffer 100 mM Sodium Acetate pH3.5, 500 mM NaCl, 0.005% Triton X-100

Elastase buffer 50 mM Tris, pH 7.5, 1 M NaCl, 0.05% Brij35

1× Caspase buffer 1 50 mM HEPES pH7.4, 100 mM NaCl, 0.01% CHAPS, 0.1 mM EDTA, 10 mM DTT 1× Caspase buffer 2 50 mM HEPES pH7.4, 1 M Na Citrate, 100 mM NaCl, 0.01% CHAPS, 0.1 mM EDTA, 10 mM DTT MMP Buffer: 50 mM HEPES (pH7.5), 10 mM CaCl2, 0.01% Brij-35, Store at 4° C. add 0.1 mg/ml BSA in buffer before use.

B. Results

B.1. Immunogenicity

Expected immunogenicity of the known MQ1 peptide of SEQ ID NO. 7 and of the MQ LEAD peptide of SEQ ID NO. 6 has been calculated.

The comparative results are depicted in FIG. 1.

As it is shown in FIG. 1, the immunogenic regions that are present in the known MQ1 peptide are no more apparent in the MQ LEAD V2R antagonist peptide.

While on MQ1 (U-Da2a), 15 potential epitopes were identified, including 6 epitopes with high scores (percentile below 10%), only 3 potential T epitopes were identified in the sequence of MQ-LEAD. These 3 potential T epitopes also have low scores (percentiles between 20 and 30%).

Then, the MQ-LEAD peptide will present a much lower risk of immunogenicity than the known MQ1 peptide.

B.2. Selectivity

Selectivity of the known MQ1 peptide for the vasopressin-2 receptor has been tested by assaying for its binding to a high number of molecules.

The results are depicted in Table 3 at the end of the present disclosure.

The results of Table 3 illustrate the selectivity of the MQ 1 peptide for the vasopressin-2 receptor.

Example 3: Pharmacology of the V2R Antagonist Peptides

A. Materials and Methods—V2R Binding Assay

Membranes from cells expressing vasopressin receptors were purchased from PERKINELMER (Courtaboeuf, France). Binding experiments were performed with $^3$H-AVP (PERKINELMER, Courtaboeuf, France) in 96-well plates. Reaction mixtures contained 50 mM Tris-HCl, pH 7.4, 10 mM MgCl$_2$ and 1 g/L BSA in a final volume of 100 μL. Plates were incubated for 3 h at room temperature. Binding reactions were stopped by filtration through a GF/C filter pre-soaked in 0.5% polyethyleneimine on a cell harvester (PERKINELMER, Courtaboeuf, France) and plates were dried. Ultimagold O (25 μl; PERKINELMER) was added to each well and samples were counted using a TopCount counter (PERKINELMER, Courtaboeuf, France) (Counting yield of 55%). Non-specific binding was measured in the presence of 1 μM AVP. A one-site inhibition mass action curve was fitted to inhibition binding data using Kaleidagraph (SYNERGY SOFTWARE, Reading, PA, USA). IC$_{50}$ values were converted to Ki for competition experiments using the Cheng-Prusoff equation (Cheng et al., Biochem. Pharmacol., 1973, 22, 3099-3108).

B. Results

Binding of a V2R Antagonist Peptide According to the Disclosure to V2R

The results are depicted in FIG. 2.

The results of FIG. 2 show that the MQ-LEAD peptide according to this disclosure has a five times increase in affinity for the vasopressin-2 receptor, as compared to the known MQ1 (U-Da2a) peptide. Even better results are obtained with the V2R antagonist peptide MQ K39A.

These results show that the V2R antagonist peptides MQ-LEAD and MQ K39A behave as a strong V2R antagonist peptides.

Example 4: In Vivo Activity of V2R Antagonists According to the Disclosure

A. Materials and Methods

A.1. In Vivo Assay of Diuresis

Sprague Dawley rats of ages between 6 and 12 weeks were acclimated in metabolic cages (Techniplast France, Lyon, France) for two days, with food and water ad libidum, before being i.p. injected (fixed volume of 1 ml) with various MQs at 3 nmol/kg dissolved in 0.9% NaCl, (French agreement number 2015082111349702v1). Urines were collected at various times, centrifuged for 30 min at 20,800 g. Urine osmolality was determined with an osmometer (Knauer, Berlin, Germany).

A.2. In Vivo Assay on an Experimental Model of Hyponatremia

Rat Model of Hyponatremia.

Specific pathogen free adult male Sprague-Dawley rats (body weight between 445 and 525 grams) were obtained from Janvier laboratories (Le Genest St. Isle, 53941, Saint Berthevin Cedex, France) and acclimatized to the animal house conditions for 1 week. We established an experimental protocol derived from a previous paper (Miyazaki T, Yamamura Y, Onogawa T, Nakamura S, Kinoshita S, Nakayama S, et al. Therapeutic effects of tolvaptan, a potent, selective nonpeptide vasopressin V2 receptor antagonist, in rats with acute and chronic severe hyponatremia. Endocrinology. 2005; 146: 3037-43.) to develop a rat hyponatremia model, approved by the French Ministry of Education and Research (n° 18604-2019010915104191). A stock solution of desmopressin (dDAVP) at 2.2 mg/mL was prepared by dissolving 5 mg of drug into physiological saline. dDAVP was administered using subcutaneous ALZET osmotic mini-pumps (model 2002, DURECT Corporation, Cupertino, CA95014, USA) previously filled with a solution of dDAVP (pumping rate of 0.47±0.02 µL/hour and mean fill volume of 233.6±4.7 µL). The dose of dDAVP (10 ng/hour) was determined in preliminary experiments. Buprenorphine (Centravet, 03120 Lapalisse, France) was administered once a day at a dose of 0.02 mg/kg, s.c. from day 0 to day 3 in order to suppress post-operative pain. Water gavage (30 mL/kg) was performed 2 times per day (at 9 am and 4 pm) in the first 3 days following ALZET pump implantation, and at 9 am at day 4. Body weight was taken every day in order to adjust for the volume of water to be administered. Rats had free access to standard rat chow, as well as water in their cages. MQ1, dissolved in physiological saline, was administered at 10 am on days 2-3-4 at 10 or 100 µg/kg (s.c. route, 0.8 mL/kg). On days 0, 2, 3 and 4, at 9 am, 400 µL of blood was collected from isoflurane-anesthetized rats from the tail vein with lithium heparinate (Sanofi-Aventis, Gentilly, France). Samples were centrifugated (4° C., 2000 g, 5 min). Sodium quantifications were performed by the Central laboratory of the ENVT, Toulouse, France, on VITROS 250/350/950/5,1 FS, 4600 and integrated system VITROS 5600 (Ortho-Clinical Diagnostics, Buckinghamshire, United Kingdom). $P < 0.05$, ANOVA multiple factors followed by Tukey's test).

B. Results

B.1. Effects of Two V2R Antagonist Peptides According to the Disclosure on Diuresis The results are depicted in FIG. 3 (FIGS. 3A and 3B). The results of FIG. 3 show that the MQ-LEAD and the MQ K39A peptides of this disclosure both increase diuresis.

B.2. Effects of V2R Antagonist Peptides According to the Disclosure on Hyponatremia.

The aim of the present study was to test the effect of a peptide derived from mambaquaretine (MQ-LEAD) a potent and selective antagonist of the V2 receptors, on DDAVP-induced hyponatremia in normal adult male rats of CD strain (Sprague Dawley).

The MQ-LEAD peptide has been validated on a rat model of hyponatremia. The schedule of the in vivo assay is depicted in FIG. 4.

The results are depicted in FIG. 5.

The results depicted I FIG. 5 showed that at D4 the effect of tolvaptan (10 mg/kg, oral route) was significantly different from values on the vehicle-treated group. The mean value for sodium in tolvaptan-treated group (137.6±3.3 mM). At D4 the plasmatic sodium concentrations of the 3 doses of MQ-LEAD (20, 60 and 200 µg/kg, s.c.) were significantly higher than the corresponding value on the vehicle-treated group. A direct comparison with the dose of tolvaptan (10 mg/kg, p.o.) suggests that MQ-LEAD could be 500 times more potent than tolvaptan. The sodium values following MQ-LEAD at 20 and 60 µg/kg on D3 and D4, although increased, were not statistically different with respect to basal values (DO)

Example 5: Inhibition of cAMP Production by V2R Antagonist Peptides of the Closure A. Materials and Methods A.1. The antagonist effects of MQ-WT, MQ-18 (K39A) and MQ-232 (MQ-LEAD) in the U2OS AVPR2A Nomad cell line stably expressing human Arginine Vasopressin were examined.

U2OS AVPR2 Nomad cell line contains U2OS cells stably expressing human Arginine Vasopressin Receptor 2A (AVPR2A) with no tag. This cell line has been designed to assay compounds or analyze their capability to modulate Arginine Vasopressin Receptor 2A (AVPR2A). When the agonist binds to AVPR2 a Gs protein is activated, which in turn, triggers a cellular response mediated by cAMP. This cellular response can be measured quantifying the increase in fluorescence intensity and its cellular distribution.

A.2. Receptor 2A (V2R). The test items were assayed at eight concentrations (in triplicate, from 1 µM to 1 nM) using 1 nM of human Arg8-Vasopressin as agonist, using a fluorescence-based assay.

Day 1. The Nomad AVPR2 U2OS cell line was thawed (2×106 cells per T25).

Day 2. The cells were maintained in DMEM-F12 supplemented with 10% FBS at 37° C. in a humidified 5% $CO_2$ atmosphere.

Day 3. The cells were plated at a concentration of 20.000 cells/well (+/−2000 cells) in 96-well plates. Cells were maintained in DMEM-F12 medium supplemented with 10% FBS during 24 h at 37° C. in a humidified 5% $CO_2$ atmosphere.

Day 4. The cells were incubated with different concentration of test compounds (1000, 333.33, 111.11, 37.04, 12.37, 4.12, 1.37 and 0.46 nM) and 1 nM of Arg8-Vasopressin dissolved in Opti-MEM for 24 hours. Opti-MEM with vehicle (water) was added to the unstimulated control cells, 1 nM of Arg8-Vasopressin to positive control cells and 1 nM of Arg8-Vasopressin with 100 nM Conivaptan to antagonism control. The experiments have been performed at least in triplicate.

Day 5. The activation of the Nomad biosensor was quantified after the formaldehyde fixation (3.7 wt. %, 20 minutes) of the cells. The nuclei were stained using DAPI (2 µg/ml) and the fluorescence was measured using a Cell Insight High-Content Bioimager from Thermofisher. To detect the DAPI, the filters used were 380/10 and 460/10 nm for excitation and emission, respectively and to detect the Nomad biosensor, the filters were 548/20 and 645/75 nm, respectively. The images were obtained with an objective of 20×, taking 9 pictures of each well. Cell quantification was performed delimitating the region of interest of the nuclei (stained with DAPI) and after quantification, the average of each triplicate was performed. Granule quantification was also performed using the Thermofisher Cellomics Scan Viewer 6.1.1. Spot detector application from Cell Software delimitated 2 regions of interest, the nuclei and cytosol. This software application quantified the number of granules per nuclei and the average of granule number per cytosol of each well was calculated. After that, the average of the triplicates was performed. Both Excel 2003 and Sigmaplot 9.0 were used for data management B. Results As it is shown in FIG. 5, V2R antagonist peptides of the present disclosures, namely the K39A peptide and the MQ-LEAD peptide, are more potent inhibitors of cAMP production, when compared to the parent MQ1 peptide (MQ-WT peptide). The V2R antagonist peptides inhibit in a dose-dependent manner the cAMP production under conditions of activation with Arg 8 Vasopressin.

The cAMP production inhibition properties of V2R antagonist peptides of the disclosure are further illustrated in Table 3 below.

TABLE 3

| Inhibition of cAMP production | | |
|---|---|---|
| | IC50, nM | Kinac*, nM |
| MQ1 ("MQ-WT") | 192 | 81 |
| U-Da2a K39A | 46.1 | 23 |
| MQ LEAD | 9.27 | 4.6 |

*Kinac: Inactivation constant: measure of the ability of the tested peptide to prevent the receptor activation, i.e. to prevent Arg8 Vasopressin to activate cAMP production.

TABLE 2

| | Protease | Enzyme Class | Enzyme Source | Substrate | Ex/Em | Co-Factor, comment etc. | Sub in RXN (uM) | Control Inhibitor |
|---|---|---|---|---|---|---|---|---|
| | | | | Specific specifications for the 65 enzymes | | | | |
| 1 | ACE1 | peptidyl-dipeptidase | Human recombinant aa30-1261 | MCA-RPPGFSAFK(Dnp)-OH | 320/405 | Buffer A | 10 | Captopril |
| 2 | ACE2 | peptidyl-dipeptidase | Human recombinant aa18-740 | MCA-YVADAPK(Dnp)-OH | 320/405 | ACE2 Buffer | 10 | ACE2 Inhibitor |
| 3 | ADAM-10 | metalloproteinase | Human recombinant aa18-672 | MCA-PLAQAV-Dpa-RSSSR-NH2 | 320/405 | Buffer Z | 10 | GM6001 |
| 4 | BACE 1 | Aspartyl Peptidase | Human recombinant aa22-460 (pro) & aa46-460 (mature), both C-terminal 10-His tag | MCA-SEVNLDAEFRK(Dnp)-RR-NH2 | 320/405 | 0.1M Sodium Acetate, pH 4.0 | 10 | B-Secretase inhibitor IV |
| 5 | Calpain 1 | Ca-Cysteine Proteinase | Human Erythrocytes | N-Succinyl-Leu-Tyr-AMC | 355/460 | Buffer B + 0.5 mM CaC12 | 10 | E64 |
| 6 | Caspase 1 | Cysteine Protease | Human recombinant aa120-404 | Ac-LEHD-AMC | 355/460 | Caspase buffer 2 | 5 | IETD-CHO |
| 7 | Caspase 2 | Cysteine Protease | Human recombinant aa150-435 | Ac-LEHD-AMC | 355/460 | Caspase buffer 2 | 5 | IETD-CHO |
| 8 | Caspase 3 | Cysteine Protease | Human recombinant | Ac-DEVD-AMC | 355/460 | Caspase buffer 1 | 5 | DEVD-CHO |
| 9 | Caspase 4 | Cysteine Protease | Human recombinant aa105-377 | Ac-LEHD-AMC | 355/460 | Caspase buffer 2 | 5 | IETD-CHO |
| 10 | Caspase 5 | Cysteine Protease | Human recombinant aa122-418 | Ac-LEHD-AMC | 355/460 | Caspase buffer 2 | 5 | IETD-CHO |
| 11 | Caspase 6 | Cysteine Protease | Human recombinant aa24-293 | Ac-DEVD-AMC | 355/460 | Caspase buffer 1 | 5 | DEVD-CHO |
| 12 | Caspase 7 | Cysteine Protease | Human recombinant aa24-303 | Ac-DEVD-AMC | 355/460 | Caspase buffer 1 | 5 | DEVD-CHO |
| 13 | Caspase 8 | Cysteine Protease | Human recombinant aa217-479 | Ac-LEHD-AMC | 355/460 | Caspase buffer 2 | 5 | IETD-CHO |
| 14 | Caspase 9 | Cysteine Protease | Human recombinant aa131-416 | Ac-LEHD-AMC | 355/460 | Caspase buffer 2 | 5 | IETD-CHO |
| 15 | Caspase 10 | Cysteine Protease | Human recombinant aa220-479 | Ac-LEHD-AMC | 355/460 | Caspase buffer 2 | 5 | IETD-CHO |
| 16 | Caspase 11 | Cysteine Protease | Mouse recombinant aa102-373 | Ac-LEHD-AMC | 355/460 | Caspase buffer 2 | 5 | IETD-CHO |
| 17 | Caspase 14 | Cysteine Protease | Human recombinant 2-242aa | Ac-WEHD-AMC | 355/460 | Caspase Buffer 2 | 5 | WEHD-CHO |
| 18 | Cathepsin B | Cysteine Protease | Human liver | Z-FR-AMC | 355/460 | Buffer B' | 10 | E64 |
| 19 | Cathepsin C | Cysteine Protease | Human recombinant aa25-463 | H-GR-AMC | 355/460 | Activate 100 ug/ml with 20 ug/ml Cathepsin | 10 | E64 |

TABLE 2-continued

Specific specifications for the 65 enzymes

| | Protease | Enzyme Class | Enzyme Source | Substrate | Ex/Em | Co-Factor, comment etc. | Sub in RXN (uM) | Control Inhibitor |
|---|---|---|---|---|---|---|---|---|
| 20 | Cathepsin D | Aspartyl Protease | Human recombinant aa21-412 | MCA-PLGL-Dap (Dnp)-AR-NH2 | 320/405 | L in 25 mM MES pH 6, 5 mM DTT, 1 h at room temp. Buffer B' AutoActivate 30 min at 37° C. CTSD buffer | 2 | Pepstatin A |
| 21 | Cathepsin E | Aspartyl Protease | Human recombinant aa18-396 | MCA-PLGL-Dap (Dnp)-AR-NH2 | 320/405 | AutoActivate 30 min at Room temp. CTSE buffer | 1,5 | Pepstatin A |
| 22 | Cathepsin G | Serin Protease | Human neutrophil | Suc-AAPF-AMC | 355/460 | Buffer C | 10 | Chymostatin |
| 23 | Cathepsin H | Cysteine Protease | Human liver | R-AMC | 355/460 | Buffer B + EDTA | 10 | E64 |
| 24 | Cathepsin L | Cysteine Protease | Human liver | Z-FR-AMC | 355/460 | Buffer L | 10 | E64 |
| 25 | Cathepsin S | Cysteine Protease | Human recombinant FL | Z-FR-AMC | 355/460 | Buffer B + EDTA | 10 | E64 |
| 26 | Cathepsin V | Cysteine Protease | Human recombinant aa18-334 | Z-FR-AMC | 355/460 | Buffer D | 10 | E64 |
| 27 | Chymase | Serin Protease | Human skin | Suc-AAPF-AMC | 355/460 | Buffer C | 10 | Chymostatin |
| 28 | Chymotrypsin | Serin Protease | Bovine pancreas | Suc-AAPF-AMC | 355/460 | Buffer C | 10 | Chymostatin |
| 29 | DPP IV | peptidyl-dipeptidase | Human recombinant aa29-766 | H-GP-AMC | 355/460 | MMP Buffer | 10 | P32/98 |
| 30 | DPP-VIII | peptidyl-dipeptidase | Human recombinant | H-GP-AMC | 355/460 | MMP Buffer | 10 | P32/98 |
| 31 | DPP-IX | peptidyl-dipeptidase | Human recombinant | H-GP-AMC | 355/460 | MMP Buffer | 10 | P32/98 |
| 32 | Elastase | Serin Protease | Human Neutrophil | MeOSuc-AAPV-AMC | 355/460 | Elastase Buffer | 10 | Sivelestat |
| 33 | Factor VIIa | Serin Protease | Human plasma | Z-VVR-AMC | 355/460 | Buffer A | 10 | PCI 27483 |
| 34 | Factor Xa | Serin Protease | Human plasma | CH₃SO₂-D-CHA-Gly-Arg-AMC-AcOH | 355/460 | Buffer A + 0.25 mg/ml BSA | 10 | Gabexate mesylate (GM) |
| 35 | Factor XIa | Serin Protease | Human plasma | (Boc-Glu(OBzl)-Ala-Arg)-MCA | 355/460 | Buffer A | 10 | Gabexate mesylate (GM) |
| 36 | HIV | Aspartyl Protease | Recombinant | Anaspec SensoLyte (Catalogue: 71127) | 340/490 | From kit | | Pepstatin A |
| 37 | Kallikrein 1 | Serin Protease | Human recombinant aa25-262 | Z-VVR-AMC | 355/460 | Activated by Thermolysin, Buffer A | 10 | Leupeptin |
| 38 | Kallikrein 5 | Serin Protease | Human recombinant aa67-293 | Z-VVR-AMC | 355/460 | Buffer A | 10 | Gabexate mesylate (GM) |
| 39 | Kallikrein 7 | Serin Protease | Human recombinant aa23-252 | MCA-RPKPVE-Nval-WRK(Dnp)-NH2 | 320/405 | Activate 0.1 mg/ml with 10 ug/ml Thermolysin in TCNB for 1 h 37° C., 50 mM EDTA to stop. KLK 7 buffer | 10 | Gabexate mesylate (GM) |
| 40 | Kallikrein 12 | Serin Protease | Human recombinant aa18-248 | BOC-VPR-AMC | 380/460 | Auto Activate 100 ug/ml in 0.1M Tris pH 8, CNB 16 h at 37° C. TCNB | 10 | Gabexate mesylate (GM) |
| 41 | Kallikrein 13 | Serin Protease | Human recombinant aa1-262 | BOC-VPR-AMC | 380/460 | Activate 100 ug/ml with 0.02 ug/ml Lysyl Endopeptidase in 0.1M Tris pH 8, 30 min at 37° C. Buffer A | 10 | Gabexate mesylate (GM) |
| 42 | Kallikrein 14 | Serin Protease | Human recombinant aa19-248 | BOC-VPR-AMC | 380/460 | Activate 0.1 mg/ml with 10 ug/ml Thermolysin in TCNB for 1 h 37° C., 50 mM | 10 | Gabexate mesylate (GM) |

TABLE 2-continued

Specific specifications for the 65 enzymes

| | Protease | Enzyme Class | Enzyme Source | Substrate | Ex/Em | Co-Factor, comment etc. | Sub in RXN (uM) | Control Inhibitor |
|---|---|---|---|---|---|---|---|---|
| 43 | Matriptase-2 | Serin Protease | Human recombinant aa78-811 | Boc--Gln-Ala-Arg-AMC | 355/460 | EDTA to stop. Buffer A 100 mM TRIS, pH 9.0, 0.5 mg/ml BSA | 10 | Gabexate mesylate (GM) |
| 44 | MMP1 | metalloproteinase | Human recombinant aa81-249 | (5-FAM/QXLTM) FRET peptide [QXL520-g-Abu-P-Cha-Abu-Smc-H-A-Dab(5-FAM)-A-K-NH2] | 485/520 | MMP Buffer | 5 | GM6001 |
| 45 | MMP2 | metalloproteinase | Human recombinant aa81-423 | (5-FAM/QXLTM) FRET peptide | 485/520 | MMP Buffer | 5 | GM6001 |
| 46 | MMP3 | metalloproteinase | Human recombinant aa83-255 | (5-FAM/QXLTM) FRET peptide | 485/520 | MMP Buffer | 5 | GM6001 |
| 47 | MMP7 | metalloproteinase | Human recombinant aa78-250 | (5-FAM/QXLTM) FRET peptide | 485/520 | MMP Buffer | 5 | GM6001 |
| 48 | MMP8 | metalloproteinase | Human recombinant aa79-249 | (5-FAM/QXLTM) FRET peptide | 485/520 | MMP Buffer | 5 | GM6001 |
| 49 | MMP9 | metalloproteinase | Human recombinant aa88-438 | (5-FAM/QXLTM) FRET peptide | 485/520 | MMP Buffer | 5 | GM6001 |
| 50 | MMP10 | metalloproteinase | Human recombinant aa82-254 | (5-FAM/QXLTM) FRET peptide | 485/520 | MMP Buffer | 5 | GM6001 |
| 51 | MMP12 | metalloproteinase | Human recombinant aa84-255 | (5-FAM/QXLTM) FRET peptide | 485/520 | MMP Buffer | 5 | GM6001 |
| 52 | MMP13 | metalloproteinase | Human recombinant aa85-255 | (5-FAM/QXLTM) FRET peptide | 485/520 | MMP Buffer | 5 | GM6001 |
| 53 | MMP14 | metalloproteinase | Human recombinant aa92-278 | (5-FAM/QXLTM) FRET peptide | 485/520 | MMP Buffer | 5 | GM6001 |
| 54 | Neprilysin | metalloproteinase | Human recombinant aa53-750 | MCA-RPPGFSAFK(Dnp)-OH | 340/405 | 50 mM Tris, pH 9.0 | 10 | Phosphoramidon |
| 55 | Papain | Cysteine Protease | Papaya Latex | Z-FR-AMC | 355/460 | B + 1 mM EDTA, Preincubate | 10 | E64 |
| 56 | Plasma Kallikrein | Serin Protease | Human recombinant aa20-638 | Z-FR-AMC | 380/460 | Activate 0.1 mg/ml with 10 ug/ml Thermolysin in TCN for 30 min 37° C., 10 mM EDTA to stop. Buffer A | 10 | Gabexate mesylate (GM) |
| 57 | Plasmin | Serin Protease | Human plasma | H-D-CHA -Ala-Arg-AMC.2AcOH | 355/460 | Buffer A | 10 | Gabexate mesylate (GM) |
| 58 | Proteinase A | Serin Protease | *Bacillus Iicheniformis* | Z-GPR-AMC | 355/460 | Buffer A | 10 | Leupeptin |
| 59 | Proteinase K | Serin Protease | Tritirachium album limber | H-D-CHA -Ala-Arg-AMC.2AcOH | 355/460 | Buffer A | 10 | Proteinase K inhibitor |
| 60 | TACE | metalloproteinase | Human recombinant aa215-671 | MCA-PLAQAV-Dpa-RSSSR-NH2 | 320/405 | Buffer Z | 10 | GM6001 |
| 61 | Thrombin alpha | Serin Protease | Human plasma | H-D-CHA -Ala-Arg-AMC.2AcOH | 355/460 | Buffer A + 2.5 mM CaCl2 + 1 mg/ml BSA | 10 | Gabexate mesylate (GM) |
| 62 | Trypsin | Serin Protease | Bovine pancreas | H-D-CHA -Ala-Arg-AMC.2AcOH | 355/460 | Buffer A | 10 | Gabexate mesylate (GM) |
| 63 | Tryptase beta 2 | Serin Protease | Human recombinant | Z-GPR-AMC | 355/460 | Unstable w/o 2M NaCl, dilute immediately before. Buffer A | 10 | Gabexate mesylate (GM) |
| 64 | Tryptase gamma 1 | Serin Protease | Human lung | Z-GPR-AMC, | 355/460 | Buffer A | 10 | Gabexate mesylate (GM) |
| 65 | Urokinase | Serin Protease | Human urine | Bz-b-Ala-Gly-Arg-AMC.AcOH | 355/460 | Buffer A | 10 | Gabexate mesylate (GM) |

TABLE 3

| | Target: | U-Da2A | Control Compound IC50 (M) | Control compound ID |
|---|---|---|---|---|
| | | | Compound IC50 (M) | |
| 1 | Caspase 1 | 3.71E−05 | 8.93E−08 | IETD-CHO |
| 2 | Caspase 2 | 4.25E−05 | 6.46E−07 | IETD-CHO |
| 3 | Caspase 3 | | 2.35E−09 | DEVD-CHO |
| 4 | Caspase 4 | | 2.18E−06 | IETD-CHO |
| 5 | Caspase 5 | >5.00E−05 | 3.83E−08 | IETD-CHO |
| 6 | Caspase 6 | >5.00E−05 | 2.65E−08 | DEVD-CHO |
| 7 | Caspase 7 | | 5.11E−09 | DEVD-CHO |
| 8 | Caspase 8 | | 2.52E−09 | IETD-CHO |
| 9 | Caspase 9 | 8.94E−06 | 5.15E−08 | IETD-CHO |
| 10 | Caspase 10 | 9.33E−06 | 2.83E−08 | IETD-CHO |
| 11 | Caspase 11 | 1.40E−05 | 9.34E−07 | IETD-CHO |
| 12 | Cathepsin B | | 5.10E−09 | E64 |
| 13 | Cathepsin C | 4.59E−05 | 5.90E−07 | E64 |
| 14 | Cathepsin G | 8.54E−06 | 2.36E−07 | Chymostatin |
| 15 | Cathepsin H | | 6.71E−08 | E64 |
| 16 | Cathepsin L | | 1.96E−09 | E64 |
| 17 | Cathepsin S | | 5.43E−09 | E64 |
| 18 | Cathepsin V | | 1.97E−08 | E64 |
| 19 | Chymase | 1.82E−05 | 1.99E−08 | Chymostatin |
| 20 | Chymotrypsin | 2.74E−06 | 3.21E−10 | Chymostatin |
| 21 | Elastase | >5.00E−05 | 2.16E−07 | Gabexate mesylate (GM) |
| 22 | FVIIa | | | Gabexate mesylate (GM) |
| 23 | FXa | | 4.47E−06 | Gabexate mesylate (GM) |
| 24 | FXIa | | 2.34E−07 | Gabexate mesylate (GM) |
| 25 | Kallikrein 1 | | 2.96E−07 | Leupeptin |
| 26 | Kallikrein 5 | 5.77E−06 | 6.97E−07 | Gabexate mesylate (GM) |
| 27 | Kallikrein 7 | 3.65E−06 | 4.65E−05 | Gabexate mesylate (GM) |
| 28 | Kallikrein 12 | | 6.54E−08 | Gabexate mesylate (GM) |
| 29 | Kallikrein 13 | | 1.18E−05 | Gabexate mesylate (GM) |
| 30 | Kallikrein 14 | | 6.72E−07 | Gabexate mesylate (GM) |
| 31 | Matriptase 2 | 1.16E−07 | 3.15E−07 | Gabexate mesylate (GM) |
| 32 | Papain | 1.76E−05 | 1.18E−10 | E64 |
| 33 | Plasma Kallikrein | 3.89E−06 | 3.03E−08 | Gabexate mesylate (GM) |
| 34 | Plasmin | | 3.44E−07 | Gabexate mesylate (GM) |
| 35 | Proteinase A | | 3.15E−05 | Leupeptin |
| 36 | Proteinase K | | 2.92E−08 | Proteinase K inhibitor |
| 37 | Thrombin A | | 3.16E−06 | Gabexate mesylate (GM) |
| 38 | Trypsin | 3.69E−06 | 1.12E−08 | Gabexate mesylate (GM) |
| 39 | Tryptase b2 | 3.63E−06 | 1.98E−08 | Gabexate mesylate (GM) |
| 40 | Tryptase g1 | >5.00E−05 | 1.01E−08 | Gabexate mesylate (GM) |
| 41 | Urokinase | | 6.14E−07 | Gabexate mesylate (GM) |

The invention claimed is:

1. A peptide comprising the amino acid sequence that is at least 80% identical to the amino acid sequence set forth below:

(SEQ ID NO: 1)
RPSX$_1$CNLPVKPGPCX$_2$GFFSAFYYSQKX$_3$NKCHSFTYGGCAGNANRFST

X$_4$EKCRRTCX$_5$X$_6$, wherein:

X$_1$ is F or G;

X$_2$ is any amino acid residue except K, R or H;

X$_3$ is T or D;

X$_4$ is I, L or E;

(i) X$_5$ is V and X$_6$ is G, or (ii) X$_5$ is G and X$_6$ is V; and wherein the alanine at position 39 of SEQ ID NO: 1 in the peptide is unsubstituted.

2. The peptide of claim 1, wherein X$_1$ is G.

3. The peptide of claim 1, wherein X$_2$ is selected from the group consisting of A, D, E, F, G, I, L, N, M, Q, S, T, V and Y.

4. The peptide of claim 1, wherein X$_3$ is D.

5. The peptide of claim 1, wherein X$_4$ is E or L.

6. The peptide of claim 1, wherein X$_4$ is L.

7. The peptide of claim 1, wherein the peptide comprises the amino acid sequence of SEQ ID NO: 1.

8. The peptide of claim 1, wherein the peptide comprises the amino acid sequence selected from the group consisting of SEQ ID NOS: 2-6.

9. The peptide of claim 1, wherein the peptide is conjugated to a detectable molecule.

10. A pharmaceutical composition comprising a peptide of claim 1 and a pharmaceutically acceptable carrier.

11. A method of inhibiting type 2 vasopressin receptor (V2R) activity in a subject in need thereof, wherein the method comprises administering to the subject a peptide of claim 8.

12. A method of treating a disease in a subject in need thereof, wherein the method comprises administering to the subject a peptide of claim 8, and wherein the disease is selected from the group consisting of euvolemic hyponatremia, hypovolemic hyponatremia polycystic kidney disease, refractory liver disease, and heart failure.

13. A method for detecting one or more cells expressing vasopressin-2 receptor, wherein the method comprises contacting the cell in vitro with a conjugate comprising a detectable molecule linked to a peptide comprising the amino acid sequence selected from the group consisting of SEQ ID NOs: 2-6.

14. A method for detecting a dysregulation of vasopressin-2 receptor expression of a cell, wherein the method comprises:

(a) contacting the cell in vitro with a conjugate comprising a detectable molecule linked to a peptide comprising the amino acid sequence selected from the group consisting of SEQ ID NOs: 2-6;

(b) measuring the expression level of vasopressin-2 receptor expression of the cell;

(c) comparing the expression level obtained in the measuring (b) with a reference expression level; and (d) determining an occurrence of a dysregulation of vasopressing-2 receptor expression.

* * * * *